(12) United States Patent
Noelle et al.

(10) Patent No.: US 7,387,271 B2
(45) Date of Patent: Jun. 17, 2008

(54) IMMUNOSTIMULATORY COMBINATIONS

(75) Inventors: Randolph J. Noelle, Plainfield, NH (US); Cory L. Ahonen, Hanover, NH (US); Ross M. Kedl, Roseville, MN (US)

(73) Assignees: 3M Innovative Properties Company, St. Paul, MN (US); Trustees of Dartmouth College, Hanover, NH (US)

( * ) Notice: Subject to any disclaimer, the term of this patent is extended or adjusted under 35 U.S.C. 154(b) by 486 days.

(21) Appl. No.: 10/748,010

(22) Filed: Dec. 30, 2003

(65) Prior Publication Data

US 2004/0141950 A1    Jul. 22, 2004

Related U.S. Application Data

(60) Provisional application No. 60/437,398, filed on Dec. 30, 2002.

(51) Int. Cl.
| | |
|---|---|
| *A61K 39/12* | (2006.01) |
| *A61K 39/02* | (2006.01) |
| *A61K 38/19* | (2006.01) |
| *A61K 39/395* | (2006.01) |
| *A61K 31/44* | (2006.01) |
| *A61K 31/435* | (2006.01) |
| *A61K 31/47* | (2006.01) |
| *C07K 14/715* | (2006.01) |

(52) U.S. Cl. .............................. 242/278.1; 424/144.1; 424/184.1; 424/204.1; 424/234.1; 424/265.1; 424/277.1; 514/2; 514/44; 514/311; 514/315

(58) Field of Classification Search .................... None
See application file for complete search history.

(56) References Cited

U.S. PATENT DOCUMENTS

| | | | |
|---|---|---|---|
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster et al. | |
| 5,268,376 A | 12/1993 | Gerster | |
| 5,346,905 A | 9/1994 | Gerster | |
| 5,352,784 A | 10/1994 | Nikolaides et al. | |
| 5,367,076 A | 11/1994 | Gerster | |
| 5,376,501 A | 12/1994 | Mariën et al. | |
| 5,389,640 A | 2/1995 | Gerster et al. | |
| 5,395,937 A | 3/1995 | Nikolaides et al. | |
| 5,446,153 A | 8/1995 | Lindstrom et al. | |
| 5,482,936 A | 1/1996 | Lindstrom | |
| 5,494,916 A | 2/1996 | Lindstrom et al. | |
| 5,525,612 A | 6/1996 | Gerster | |
| 5,605,899 A | 2/1997 | Gerster et al. | |
| 5,693,811 A | 12/1997 | Lindstrom | |
| 5,708,142 A | 1/1998 | Goeddel et al. | |
| 5,741,908 A | 4/1998 | Gerster et al. | |
| 5,756,747 A | 5/1998 | Gerster | |
| 5,939,090 A | 8/1999 | Beaurline et al. | |
| 6,028,076 A | 2/2000 | Hirota et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,113,918 A | 9/2000 | Johnson et al. | |
| 6,194,388 B1 | 2/2001 | Krieg et al. | |
| 6,194,425 B1 | 2/2001 | Gerster et al. | |
| 6,200,592 B1 | 3/2001 | Tomai et al. | |
| 6,207,646 B1 | 3/2001 | Krieg et al. | |
| 6,239,116 B1 | 5/2001 | Krieg et al. | |
| 6,245,776 B1 | 6/2001 | Skwierczynski et al. | |
| 6,303,347 B1 | 10/2001 | Johnson et al. | |
| 6,323,200 B1 | 11/2001 | Gerster et al. | |
| 6,329,381 B1 | 12/2001 | Kurimoto et al. | |
| 6,331,539 B1 | 12/2001 | Crooks et al. | |
| 6,339,068 B1 | 1/2002 | Krieg et al. | |
| 6,376,501 B1 | 4/2002 | Isobe et al. | |
| 6,376,669 B1 | 4/2002 | Rice et al. | |
| 6,387,938 B1 | 5/2002 | Mizuguchi et al. | |
| 6,406,705 B1 | 6/2002 | Davis et al. | |
| 6,426,334 B1 | 7/2002 | Agrawal et al. | |
| 6,440,992 B1 | 8/2002 | Gerster et al. | |
| 6,451,810 B1 | 9/2002 | Coleman et al. | |
| 6,476,000 B1 | 11/2002 | Agrawal | |
| 6,514,985 B1 | 2/2003 | Gerster et al. | |

(Continued)

FOREIGN PATENT DOCUMENTS

EP      0 394 026      10/1990

(Continued)

OTHER PUBLICATIONS

Beutler et al., Genetic analysis of host resistance:Toll-like receptor signalling and immunity at large, Ann. Rev. Immunol., 24:353-89, 2006.*

(Continued)

*Primary Examiner*—Lorraine Spector
*Assistant Examiner*—Claire Kaufman

(57) ABSTRACT

The present invention provides immunostimulatory combinations. Generally, the immunostimulatory combinations include a TLR agonist and a TNF/R agonist. Certain immunostimulatory combinations also may include an antigen.

77 Claims, 10 Drawing Sheets

U.S. PATENT DOCUMENTS

| | | | |
|---|---|---|---|
| 6,518,265 | B1 | 2/2003 | Kato et al. |
| 6,518,280 | B2 | 2/2003 | Gerster et al. |
| 6,525,028 | B1 | 2/2003 | Johnson et al. |
| 6,525,064 | B1 | 2/2003 | Dellaria et al. |
| 6,541,485 | B1 | 4/2003 | Crooks et al. |
| 6,545,016 | B1 | 4/2003 | Dellaria et al. |
| 6,545,017 | B1 | 4/2003 | Dellaria et al. |
| 6,558,951 | B1 | 5/2003 | Tomai et al. |
| 6,573,273 | B1 | 6/2003 | Crooks et al. |
| 6,649,172 | B2 | 11/2003 | Johnson |
| 6,656,938 | B2 | 12/2003 | Crooks et al. |
| 6,660,735 | B2 | 12/2003 | Crooks et al. |
| 6,660,747 | B2 | 12/2003 | Crooks et al. |
| 6,664,260 | B2 | 12/2003 | Charles et al. |
| 6,664,264 | B2 | 12/2003 | Dellaria et al. |
| 6,664,265 | B2 | 12/2003 | Crooks et al. |
| 6,667,312 | B2 | 12/2003 | Bonk et al. |
| 6,670,372 | B2 | 12/2003 | Charles et al. |
| 6,677,347 | B2 | 1/2004 | Crooks et al. |
| 6,677,348 | B2 | 1/2004 | Heppner et al. |
| 6,677,349 | B1 | 1/2004 | Griesgraber |
| 6,683,088 | B2 | 1/2004 | Crooks et al. |
| 2002/0016332 | A1 | 2/2002 | Slade |
| 2002/0055517 | A1 | 5/2002 | Smith |
| 2002/0058674 | A1 | 5/2002 | Hedenstrom et al. |
| 2002/0110840 | A1 | 8/2002 | Tomai et al. |
| 2003/0022302 | A1 | 1/2003 | Lewis et al. |
| 2003/0133913 | A1 | 7/2003 | Tomai et al. |
| 2003/0139364 | A1 | 7/2003 | Krieg et al. |
| 2003/0144283 | A1 | 7/2003 | Coleman et al. |
| 2003/0199461 | A1 | 10/2003 | Averett et al. |
| 2004/0010007 | A1 | 1/2004 | Dellaria et al. |
| 2004/0014779 | A1 | 1/2004 | Gorden et al. |
| 2004/0023870 | A1 | 2/2004 | Dedera et al. |

FOREIGN PATENT DOCUMENTS

| | | |
|---|---|---|
| EP | 1 104 764 A1 | 6/2001 |
| JP | 9-208584 | 8/1997 |
| JP | 11-80156 | 3/1999 |
| JP | 11-222432 | 8/1999 |
| JP | 2000-247884 | 9/2000 |
| WO | WO 00/47719 A2 | 8/2000 |
| WO | WO 00/75304 A1 | 12/2000 |
| WO | WO 00/76505 A1 | 12/2000 |
| WO | WO 00/76518 A1 | 12/2000 |
| WO | WO 01/74343 A2 | 10/2001 |
| WO | WO 02/36592 A1 | 5/2002 |
| WO | WO 02/46188 A2 | 6/2002 |
| WO | WO 02/46189 A2 | 6/2002 |
| WO | WO 02/46190 A2 | 6/2002 |
| WO | WO 02/46191 A2 | 6/2002 |
| WO | WO 02/46192 A2 | 6/2002 |
| WO | WO 02/46193 A2 | 6/2002 |
| WO | WO 02/46194 A2 | 6/2002 |
| WO | WO 02/46749 A2 | 6/2002 |
| WO | WO 02/072032 | 9/2002 |
| WO | WO 02/085905 A1 | 10/2002 |
| WO | WO 02/102377 A1 | 12/2002 |
| WO | WO 03/020889 A2 | 3/2003 |
| WO | WO 03/043572 A2 | 5/2003 |
| WO | WO 03/045391 A1 | 6/2003 |
| WO | WO 03/089602 | 10/2003 |
| WO | WO 03/103584 A2 | 12/2003 |

OTHER PUBLICATIONS

Fitzgerald et al., The Cytokine Facts Book, 2nd Ed., (Academic Press: San Diego), 2001, p. 27.*

Melief et al., Effective therapeutic anticancer vaccines based on precision guiding of cytolytic T lymphocytes, Immunol. Rev. 188:177-182, Oct. 2002.*

Ito et al., Interferon-alpha and interleukin-12 are induced differentially by Toll-like receptor 7 ligands in human blood dendritic cell subsets, J. Exp. Med. 195(11):1507-15-12, Jun. 3, 2002.*

Krug et al. Toll-like receptor expression reeals CpG DNA as a unique microbial stimulus for plasmacytoid dendritic cells which synergizes with CD40 ligand to induce high amounts of IL-12, Eur. J. Immunol. 31:3026-3037, Oct. 2001.*

Edwards et al., Microbial recognition via toll-like receptor-dependent and -independent pathways determines the cytokine resonse of murine dendritic cell subsets to Dc40 triggering, J. Immunol. 169:3652-3660, Oct. 1, 2002.*

Ahonen et al., Combined TLR and CD40 tirggering induces potent CD8+ T cell expansion wih variable dependence on type I INF, J. Exp. Med. 199(6):775-784, Mar. 15, 2004.*

Myers et al., Effector CD8 T cells possess suppressor function after 4-1BB and toll-like receptor triggering, Proc. Natl. Acad. Sci. 100(9):5348-5353, Apr. 29, 2003.*

Sabroe et al., Review: Toll-like receptors: their role in allergy and non-allergic inflammatory response, Clin. Exp. Allergy, 32:984-989, 2002.*

Gantner et al., CD-40-dependent and -independent activation of human tonsil B cells by CpG oligodeoxynucleotides, Eur. J. Immunol. 33:1576-1585, Jun. 2003.*

Singh et al., Recent advances in vaccine adjuvants, Pharm. Res. 19(6):715-728, Jun. 2002.*

Vonderheide et al., Phase I study of recombinant human CD40 ligand in cancer patients, J. Clin. Oncol. 19(13):3280-3287, Jul. 1, 2001.*

Forteneau et al., Huamn immunodeficiency virust type 1 activates plasmacytoid dendritic cells and concomitantly induces the bystander maturation of myeloid dendritic cells, J. Virol. 78(10): 5223-32, 2004, Abstract only.*

Forteneau et al., Activation of influenza virus-specific CD4+ and CD8+ T cells: a new role for plasmacytoid dendritic cells in adaptive immunity, Blood, 101(9):3520-6, May 2003, Abstract only.*

Gorden et al., "Synthetic TLR Agonists Reveal Functional Differences between Human TLR7 and TLR8", The Journal of Immunology, 2005, vol. 174, pp. 1259-1268.

Sauder et al., "Randomized, Single-Blind, Placebo-Controlled Study of Topical Application of the Immune Response Modulator Resiquimod in Healthy Adults", Antimicrobial Agents and Chemotherapy, Dec. 2003, vol. 47, No. 12, pp. 3846-3852.

Akira S. et al., "Recognition of pathogen-associated molecular patterns by TLR family", Immunology Letters, 2003, vol. 85, pp. 85-95.

Ozinsky A. et al., "The repertoire for pattern recognition of pathogens by the innate immune system in defined by cooperation between Toll-like receptors", Proc. Nat. Acad. Sci., Dec. 2000, vol. 97, No. 25, pp. 13766-13771.

Testerman, et al., "Cytokine Induction by the Immunomodulators Imiquimod and S-27609", Journal of Leukocyte Biology, vol. 58, pp. 365-372, Sep. 1995.

Chollet, et al, "Development of a Topically Active Imiquimod Formulation", Pharmaceutical Development and Technology, 4(1), pp. 35-43 (1999).

Brassard et al.; "Interferon-α as an immunotherapeutic protein"; Journal of Leukocyte Biology; vol. 71; Apr. 2002; pp. 565-581.

Izumi et al.; "1H-imidazo[4,5-c]quinoline Derivatives as Novel Potent TNF-α Suppressors: Synthesis and Structure-Activity Relationship of 1-, 2-and 4-Substituted 1H-imidazo[4,5-c]quinolines or 1H-imidazo[4,5-c]pyridines"; Bioorganic and Medicinal Chemistry, vol. 11, pp. 2541-2550 (2003).

Hornung et al., "Quantitative Expression of Toll-Like Receptor 1-10 mRNA in Cellular Subsets of Human Peripheral Blood Mononuclear Cells and Sensitivity to CpG Oligodeoxynucleotides[1]", The Journal of Immunology, 2002, 168; pp. 4531-4537.

Hemmi et al., "Small anti-viral compounds activate immune cells via the TLR7 MyD88-dependent Signaling pathway", Nature Immunology, vol. 3, No. 2; Feb. 2002; pp. 196-200.

Medzhitov, "Toll-Like Receptors and Innate Immunity", Nature Reviews Immunology, vol. 1; Nov. 2001, pp. 135-145.

Jurk et al. "Human TLR7 and TLR8 independently confer responsiveness to the antiviral compound R-848", *Nature Immunology*, Jun. 2002, vol. 3, No. 6; p. 1.

Akira et al., "Toll-like receptors: critical proteins linking innate and acquired immunity", *Nature Immunology*, Aug. 2001, vol. 2, No. 8; pp. 675-680.

Heil et al.; "Synthetic immunostimulatory compounds activate immune cells via TLR7 and TLR8"; 33th Annual Meeting of the Deutsche Gessellschaft für Immunologie, Marburg 2002—Abstract C.6.

Takeuchi et al.; "Discrimination of bacterial lipoproteins by Toll-like receptor 6", International Immunology, Mar. 2001, vol. 13, No. 7, pp. 933-940.

Maxwell et al,; "Contrasting the Roles of Costimulation and the Natural Adjuvant Lipopolysaccharide During the Induction of T Cell Immunity", *J. Immunol.*, May 2002; vol. 168, pp. 4372-4381.

Maxwell et al, Danger and OX40 Receptor Signaling Synergize to Enhance Memory T Cell Survival by Inhibiting Peripheral Deletion, *J. Immunol.*, Jan. 2000; vol. 164, pp. 107-112.

Lamprecht et al.; "Heterogeneity of CD4+ and CD8+ Memory T Cells in Localized and Generalized Wegener's Granulomatosis", *Arthritis Res. and Ther.*, 2003; vol. 5, pp. R25-R31.

Mackay,; "Dual Personality of Memory T cells", *Nature*, 1999; vol. 401, pp. 659-660.

Weninger et al,; Migratory Properties of Naïve, Effector, and Memory CD8+ T Cell, *J. Exp. Med.*, Oct. 2001; vol. 194, No. 7, pp. 953-966.

Faint et al,; "Memory T Cells Constitute a Subset of the Human CD8+CD45RA+ Pool with Distinct Phenotypic and Migratory Characteristics", *J. Immunol.*, 2001, vol. 167, pp. 212-220.

Kedl et al.; "CD40 Stimulation Accelerates Deletion of Tumor-Specific CD8+ T Cells in the Absence of Tumor-Antigen Vaccination", *Proc. Nat. Acad. Sci.*, Sep. 2001; vol. 98, No. 19, pp. 10811-10816.

Kedl et al, "T Cells Compete for Access to Antigen-Bearing Antigen-Presenting Cells", *J. Exp. Med.*, vol. 192, No. 8, pp. 1105-1113.

U. Hasan et al.; "Human TLR10 Is a Functional Receptor, Expressed by B Cells and Plasmacytoid Dendritic Cells, Which Activates Gene Transcription through MyD88[1]"; *The Journal of Immunology*; pp. 2942-2950.

\* cited by examiner

US 7,387,271 B2

IMMUNOSTIMULATORY COMBINATIONS

CROSS-REFERENCE TO RELATED APPLICATION

This application claims priority to U.S. Provisional Patent Application No. 60/437,398, filed Dec. 30, 2002.

BACKGROUND OF THE INVENTION

There has been a major effort in recent years, with significant success, to discover new drug compounds that act by stimulating certain key aspects of the immune system, as well as by suppressing certain other aspects (see, e.g., U.S. Pat. Nos. 6,039,969 and 6,200,592). These compounds, referred to herein as immune response modifiers (IRMs), appear to act through basic immune system mechanisms known as Toll-like receptors (TLRs) to induce selected cytokine biosynthesis. They may be useful for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), and $T_H2$-mediated diseases (e.g., asthma, allergic rhinitis, atopic dermatitis, multiple sclerosis), and are also useful as vaccine adjuvants.

Many of the IRM compounds are small organic molecule imidazoquinoline amine derivatives (see, e.g., U.S. Pat. No. 4,689,338), but a number of other compound classes are known as well (see, e.g., U.S. Pat. Nos. 5,446,153; 6,194,425; and 6,110,929) and more are still being discovered. Other IRMs have higher molecular weights, such as oligonucleotides, including CpGs (see, e.g., U.S. Pat. No. 6,194,388).

In view of the great therapeutic potential for IRMs, and despite the important work that has already been done, there is a substantial ongoing need to expand their uses and therapeutic benefits.

SUMMARY OF THE INVENTION

In one aspect, the invention provides immunostimulatory combinations that include a TLR agonist and a TNF/R agonist, each in an amount that, in combination with the other, is effective for increasing the immune response by a subject against an antigen. In some embodiments, the immunostimulatory combination can further include an antigen in an amount that, in combination with the other components of the combination, is effective for inducing an immune response by a subject against the antigen.

In another aspect, the present invention provides a method of inducing a $T_H1$ immune response in a subject. The method includes co-administering to the subject a TLR agonist and a TNF/R agonist, each in an amount that, when in combination with the other, is effective to induce a $T_H1$ immune response. In some embodiments, the method further includes co-administering an antigen in an amount effective to induce the subject to generate an immune response against the antigen.

In another aspect, the present invention provides a method of activating antigen-specific CD8+ T cells in a subject. The method includes co-administering to the subject a TLR agonist and a TNF/R agonist, each in an amount that, in combination with the other, is effective to activate CD8+ T cells. In some embodiments, the method further includes co-administering an antigen in an amount effective to induce the subject to generate an immune response against the antigen. In some embodiments, activating CD8+ T cells can include expansion of CD8+ effector T cells. In alternative embodiments, activating CD8+ T cells can include generating CD8+ memory T cells.

In another aspect, the present invention provides a method of activating antigen-specific memory CD8+ T cells in a subject having prior exposure to an antigen. The method includes administering to the subject the antigen in an amount effective to induce antigen-specific CD8+ memory T cells to become activated, thereby generating antigen-specific CD8+ effector T cells. In some embodiments, the method further includes co-administering a TLR agonist in an amount effective to induce antigen-specific CD8+ memory T cells to become activated, thereby generating antigen-specific CD8+ effector T cells.

In another aspect, the present invention provides a method of treating a condition in a subject. The method includes co-administering to the subject a TLR agonist and a TNF/R agonist, each administered in an amount that, when in combination with the other, is effective for stimulating a cell-mediated immune response. In some embodiments, the method further includes co-administering an antigen associated with the condition in an amount effective for inducing a cell-mediated immune response.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1:
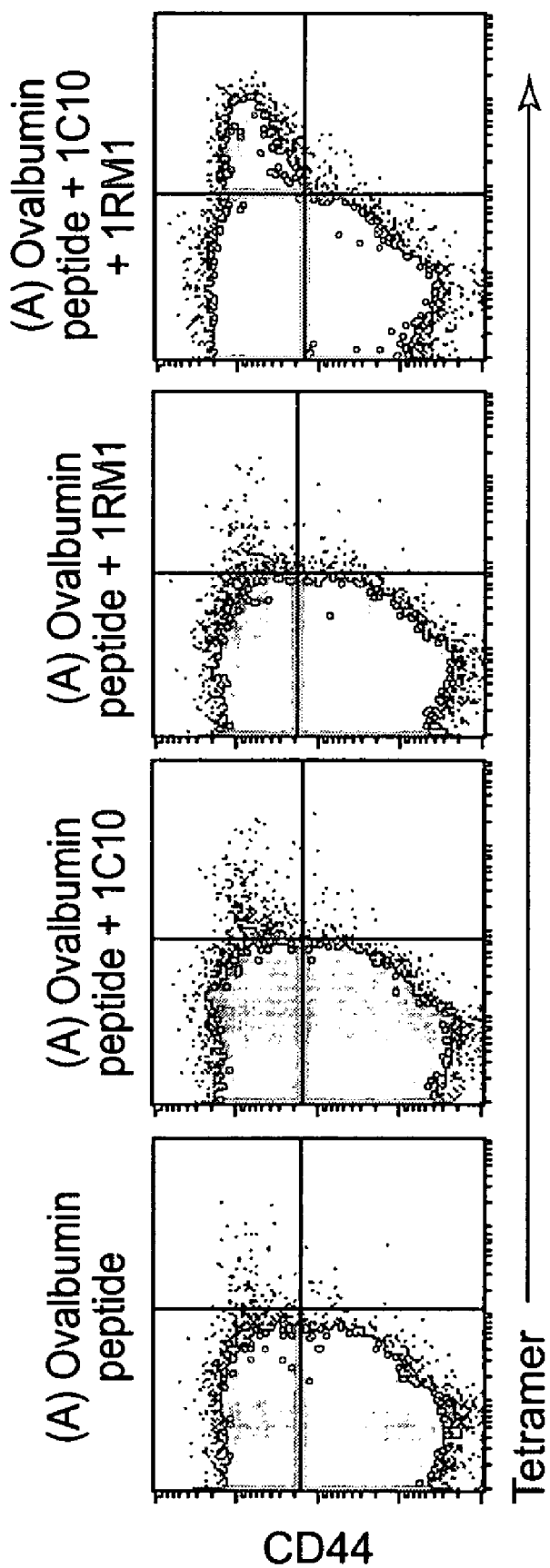
FIG. 1 shows flow cytometry data showing the results of Example 1.

The present invention provides immunostimulatory combinations and therapeutic and/or prophylactic methods that include administering an immunostimulatory combination to a subject.

In general, the immunostimulatory combinations can provide an increased immune response compared to other immunostimulatory combinations and/or compositions. Thus, methods and immunostimulatory combinations of the invention can improve the efficacy of certain immunological treatments and/or provide effective treatment while using less of a component of the combination. This may be desirable if a particular component, while useful for generating a desired immunological response, is expensive, difficult to obtain, or generates undesirable side effects.

As used herein, the following terms shall have the meanings set forth:

"Agonist" refers to a compound that, in combination with a receptor, can produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that the other compound directly binds to the receptor. An agonist may be referred to as an agonist of a particular receptor or family of receptors (e.g., a TLR agonist or a TNF/R agonist).

"Antigen" refers to any substance that is capable of being the target of an immune response. An antigen may be the target of, for example, a cell-mediated and/or humoral immune response raised by a subject organism. Alternatively, an antigen may be the target of a cellular immune response (e.g., immune cell maturation, production of cytokines, production of antibodies, etc.) when contacted with immune cells.

"Co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., cytokine production, activation of a certain cell population, etc.) persists at the treatment site until one or more additional components are administered to the treatment site. Thus, a co-administered combination can, in certain circumstances, include components that never exist in a chemical mixture with one another.

"Immunostimulatory combination" refers to any combination of components that can be co-administered to provide a therapeutic and/or prophylactic immunostimulatory effect. The components of an immunostimulatory combination can include, but are not limited to, TLR agonists, TNF/R agonists, antigens, adjuvants, and the like.

"Mixture" refers to any mixture, aqueous or non-aqueous solution, suspension, emulsion, gel, cream, or the like, that contains two or more components. The components may be, for example, two immunostimulatory components that, together, provide an immunostimulatory combination. The immunostimulatory components may be any combination of one or more antigens, one or more adjuvants, or both. For example, a mixture may include two adjuvants so that the mixture forms an adjuvant combination. Alternatively, a mixture may include an adjuvant combination and an antigen so that the mixture forms a vaccine.

"Synergy" and variations thereof refer to activity (e.g., immunostimulatory activity) of administering a combination of compounds that is greater than the additive activity of the compounds if administered individually.

"TLR" generally refers to any Toll-like receptor of any species of organism. A specific TLR may be identified with additional reference to species of origin (e.g., human, murine, etc.), a particular receptor (e.g., TLR6, TLR7, TLR8, etc.), or both.

"TLR agonist" refers to a compound that acts as an agonist of a TLR. Unless otherwise indicated, reference to a TLR agonist compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers. Also, a compound may be identified as an agonist of one or more particular TLRs (e.g., a TLR7 agonist, a TLR8 agonist, or a TLR7/8 agonist).

"TNF/R" generally refers to any member of either the Tumor Necrosis Factor (TNF) Superfamily or the Tumor Necrosis Factor Receptor (TNFR) Superfamily. The TNF Superfamily includes, for example, CD40 ligand, OX40 ligand, 4-1BB ligand, CD27, CD30 ligand (CD153), TNF-$\alpha$, TNF-$\beta$, RANK ligand, LT-$\alpha$, LT-$\beta$, GITR ligand, and LIGHT. The TNFR Superfamily includes, for example, CD40, OX40, 4-1BB, CD70 (CD27 ligand), CD30, TNFR2, RANK, LT-$\beta$R, HVEM, GITR, TROY, and RELT. "TNF/R agonist" refers to a compound that acts as an agonist of a member of either the TNF Superfamily or the TNFR Superfamily. Unless otherwise indicated, reference to a TNF/R agonist compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers. Also, a compound may be identified as an agonist of a particular member of either superfamily (e.g., a CD40 agonist).

"Treatment site" refers to the site of a particular treatment. Depending upon the particular treatment, the treatment site may be an entire organism (e.g., a systemic treatment) or any portion of an organism (e.g., a localized treatment).

"Type I interferon" refers, collectively, to IFN-$\alpha$, IFN-$\beta$, or any mixture or combination thereof.

"Vaccine" refers to a pharmaceutical composition that includes an antigen. A vaccine may include components in addition to the antigen such as, for example, one or more adjuvants, a carrier, etc.

In one aspect, the invention provides immunostimulatory combinations that include a TLR agonist and a TNF/R agonist. Each component may, by itself, possess a certain immunostimulatory activity. In many cases, the combination of components can provide greater immunostimulatory activity than either component can provide alone. In certain cases, the combination of components can provide synergistic immunostimulatory activity.

In certain embodiments, immunostimulatory combinations of the invention may be used to induce a $T_H1$ immune response in a subject to which the immunostimulatory combination is administered. As used herein, "inducing a $T_H1$ immune response" can include instances in which the immunostimulatory combination induces a mixed $T_H1/T_H2$ response. In certain embodiments, however, the immunostimulatory combinations can induce a $T_H1$ immune response with little or substantially no induction of a $T_H2$ immune response.

In some embodiments, immunostimulatory combinations of the invention may be used as an immunostimulatory adjuvant, i.e., combined with one or more antigens, either with or without additional adjuvants. Thus, in some cases, an immunostimulatory combination may form a vaccine. In other cases, an immunostimulatory combination may serve as an adjuvant that may be used in connection with a vaccine.

As shown in the Examples that follow, an immunostimulatory combination that includes a TLR agonist and a TNF/R agonist can enhance the expansion of activated CD8$^+$ T cells, the generation of memory CD8$^+$ T cells, or both. Thus, methods and immunostimulatory combinations of the invention can enhance antigen-specific cell-mediated immunity in a subject that receives the immunostimulatory combination or treatment according to a method described in detail below.

The TLR agonist may be an agonist of any TLR desirable for a particular application. TLRs have been identified in various mammalian species including, for example, humans, guinea pigs, and mice. The TLR agonist may be an agonist of any TLR (e.g., TLR6, TLR7, TLR8, etc.) from any species. In some embodiments, the TLR agonist is an agonist of a human TLR. In many cases, the TLR is a TLR from the organism to which the immunostimulatory combination will be administered, although such a correlation is not necessary.

Certain TLRs are known to bind certain pathogen-associated ligands. In some cases the ligands are pathogen-derived, while in other cases the ligands are subject-derived. For example, TLR3 recognizes polyinosinic-polycytidylic acid (polyIC), a "mimic" of double-stranded viral RNA; TLR4 recognizes lipopolysaccharide (LPS) of many Gram-negative bacteria; TLR5 binds certain flagellins; and TLR9 binds certain CpG oligonucleotides. Certain small molecule IRM compounds are known to be agonists of one or more TLRs including, for example, TLR6, TLR7, and TLR8.

In some embodiments, the TLR agonist may be an agonist of at least one of TLR6, TLR7, TLR8, and TLR9. In certain embodiment, the TLR agonist can be an agonist of TLR7 and/or TLR8. In alternative embodiments, the TLR agonist may be a TLR8-selective agonist. In other alternative embodiments, the TLR agonist can be a TLR7-selective agonist.

As used herein, the term "TLR8-selective agonist" refers to any compound that acts as an agonist of TLR8, but does not act as an agonist of TLR7. A "TLR7-selective agonist" refers to a compound that acts as an agonist of TLR7, but does not act as an agonist of TLR8. A "TLR7/8 agonist" refers to a compound that acts as an agonist of both TLR7 and TLR8.

A TLR8-selective agonist or a TLR7-selective agonist may act as an agonist for the indicated TLR and one or more of TLR1, TLR2, TLR3, TLR4, TLR5, TLR6, TLR9, or TLR10. Accordingly, while "TLR8-selective agonist" may refer to a compound that acts as an agonist for TLR8 and for no other TLR, it may alternatively refer to a compound that acts as an agonist of TLR8 and, for example, TLR6. Similarly, "TLR7-selective agonist" may refer to a compound that acts as an agonist for TLR7 and for no other TLR, but it may alternatively refer to a compound that acts as an agonist of TLR7 and, for example, TLR6.

The TLR agonism for a particular compound may be assessed in any suitable manner. For example, assays for detecting TLR agonism of test compounds are described, for example, in U.S. Patent Publication No. 2004/0132079 and recombinant cell lines suitable for use in such assays are described, for example, in U.S. Patent Publication No. 2004/0197865.

Regardless of the particular assay employed, a compound can be identified as an agonist of a particular TLR if performing the assay with a compound results in at least a threshold increase of some biological activity mediated by the particular TLR. Conversely, a compound may be identified as not acting as an agonist of a specified TLR if, when used to perform an assay designed to detect biological activity mediated by the specified TLR, the compound fails to elicit a threshold increase in the biological activity. Unless otherwise indicated, an increase in biological activity refers to an increase in the same biological activity over that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR agonism of a compound in a particular assay.

The precise threshold increase of TLR-mediated biological activity for determining whether a particular compound is or is not an agonist of a particular TLR in a given assay may vary according to factors known in the art including but not limited to the biological activity observed as the end-point of the assay, the method used to measure or detect the endpoint of the assay, the signal-to-noise ratio of the assay, the precision of the assay, and whether the same assay is being used to determine the agonism of a compound for multiple TLRs. Accordingly it is not practical to set forth generally the threshold increase of TLR-mediated biological activity required to identify a compound as being an agonist or a non-agonist of a particular TLR for all possible assays. Those of ordinary skill in the art, however, can readily determine the appropriate threshold with due consideration of such factors.

Assays employing HEK293 cells transfected with an expressible TLR structural gene may use a threshold of, for example, at least a three-fold increase in a TLR-mediated biological activity (e.g., NFκB activation) when the compound is provided at a concentration of, for example, from about 1 μM to about 10 μM for identifying a compound as an agonist of the TLR transfected into the cell. However, different thresholds and/or different concentration ranges may be suitable in certain circumstances. Also, different thresholds may be appropriate for different assays.

In certain embodiments, the TLR agonist can be a natural agonist of a TLR or a synthetic IRM compound. IRM compounds include compounds that possess potent immunomodulating activity including but not limited to antiviral and antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain $T_H2$ cytokines, such as IL-4 and IL-5. Additionally, some IRM compounds are said to suppress IL-1 and TNF (U.S. Pat. No. 6,518,265).

Certain IRMs that are useful as TLR agonists in immunostimulatory combinations of the invention are small organic molecules (e.g., molecular weight less than about 1000 Daltons, and less than about 500 Daltons in some cases), as opposed to large biological molecules such as proteins, peptides, and the like. Certain small molecule IRM compounds are disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784;

5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,545,016; 6,545,017; 6,558,951; and 6,573,273; European Patent 0 394 026; U.S. Patent Publication No. 2002/0055517; and International Patent Publication Nos. WO 01/74343; WO 02/46188; WO 02/46189; WO 02/46190; WO 02/46191; WO 02/46192; WO 02/46193; WO 02/46749 WO 02/102377; WO 03/020889; WO 03/043572 and WO 03/045391.

Additional examples of small molecule IRMs include certain purine derivatives (such as those described in U.S. Pat. No. 6,376,501, and 6,028,076), certain imidazoquinoline amide derivatives (such as those described in U.S. Pat. No. 6,069,149), certain benzimidazole derivatives (such as those described in U.S. Pat. No. 6,387,938), and certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/085905).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG and are described, for example, in International Patent Publication No. WO 00/75304.

Small molecule IRM compounds suitable for use as a TLR agonist in immunostimulatory combinations of the invention include compounds having a 2-aminopyridine fused to a five membered nitrogen-containing heterocyclic ring. Such compounds include, for example, imidazoquinoline amines including but not limited to substituted imidazoquinoline amines such as, for example, aminoalkyl-substituted imidazoquinoline amines, amide-substituted imidazoquinoline amines, sulfonamide-substituted imidazoquinoline amines, urea-substituted imidazoquinoline amines, aryl ether-substituted imidazoquinoline amines, heterocyclic ether-substituted imidazoquinoline amines, amido ether-substituted imidazoquinoline amines, sulfonamido ether-substituted imidazoquinoline amines, urea-substituted imidazoquinoline ethers, and thioether-substituted imidazoquinoline amines; tetrahydroimidazoquinoline amines including but not limited to amide-substituted tetrahydroimidazoquinoline amines, sulfonamide-substituted tetrahydroimidazoquinoline amines, urea-substituted tetrahydroimidazoquinoline amines, aryl ether-substituted tetrahydroimidazoquinoline amines, heterocyclic ether-substituted tetrahydroimidazoquinoline amines, amido ether-substituted tetrahydroimidazoquinoline amines, sulfonamido ether-substituted tetrahydroimidazoquinoline amines, urea-substituted tetrahydroimidazoquinoline ethers, and thioether-substituted tetrahydroimidazoquinoline amines; imidazopyridine amines including but not limited to amide-substituted imidazopyridine amines, sulfonamido-substituted imidazopyridine amines, urea-substituted imidazopyridine amines; aryl ether-substituted imidazopyridine amines, heterocyclic ether-substituted imidazopyridine amines, amido ether-substituted imidazopyridine amines, sulfonamido ether-substituted imidazopyridine amines, urea-substituted imidazopyridine ethers, and thioether-substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; and thiazolonaphthyridine amines.

In certain embodiments, the TLR agonist may be an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

In certain embodiments, the TLR agonist can be a sulfonamide-substituted imidazoquinoline amine. In alternative embodiments, the TLR agonist can be a urea-substituted imidazoquinoline ether. In another alternative embodiment, the TLR agonist can be an aminoalkyl-substituted imidazoquinoline amine.

In one particular embodiment, the TLR agonist is 4-amino-α,α,2-trimethyl-1H-imidazo[4,5-c]quinolin-1-ethanol. In an alternative particular embodiment, the TLR agonist is N-(2-{2-[4-amino-2-(2-methoxyethyl)-1H-imidazo[4,5-c]quinolin-1-yl]ethoxy}ethyl)-N-methylmorpholine-4-carboxamide. In another alternative embodiment, the TLR agonist is 1-(2-amino-2-methylpropyl)-2-(ethoxymethyl)-1H-imidazo[4,5-c]quinolin-4-amine. In another alternative embodiment, the TLR agonist is N-[4-(4-amino-2-ethyl-1H-imidazo[4,5-c]quinolin-1-yl)butyl]methanesulfonamide. In yet another alternative embodiment, the TLR agonist is N-[4-(4-amino-2-propyl-1H-imidazo[4,5-c]quinolin-1-yl)butyl]methanesulfonamide.

In certain alternative embodiments, the TLR agonist may be a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

As used herein, a substituted imidazoquinoline amine refers to an aminoalkyl-substituted imidazoquinoline amine, an amide-substituted imidazoquinoline amine, a sulfonamide-substituted imidazoquinoline amine, a urea-substituted imidazoquinoline amine, an aryl ether-substituted imidazoquinoline amine, a heterocyclic ether-substituted imidazoquinoline amine, an amido ether-substituted imidazoquinoline amine, a sulfonamido ether-substituted imidazoquinoline amine, a urea-substituted imidazoquinoline ether, or a thioether-substituted imidazoquinoline amines. As used herein, substituted imidazoquinoline amines specifically and expressly exclude 1-(2-methylpropyl)-1H-imidazo[4,5-c]quinolin-4-amine and 4-amino-α,α-dimethyl-2-ethoxymethyl-1H-imidazo[4,5-c]quinolin-1-ethanol.

The TNF/R agonist may be any suitable agonist of any member of either the TNF Superfamily or the TNFR Superfamily. In many cases, a member of one Superfamily can be an agonist of a complementary member of the other Superfamily. For example, CD40 ligand (a member of the TNF Superfamily) can act as an agonist of CD40 (a member of the TNFR Superfamily), and CD40 can act as an agonist of CD40 ligand. Thus, suitable TNF/R agonists include, for example, CD40 ligand, OX40 ligand, 4-1BB ligand, CD27, CD30 ligand (CD153), TNF-α, TNF-β, RANK ligand, LT-α, LT-β, GITR ligand, LIGHT, CD40, OX40, 4-1BB, CD70 (CD27 ligand), CD30, TNFR2, RANK, LT-βR, HVEM, GITR, TROY, and RELT. Additionally, suitable TNF/R agonists include certain agonistic antibodies raised against a TNF/R (e.g., IC10 and FGK4.5, each of which was raised against mouse CD40).

The TLR agonist and TNF/R agonist are provided (or administered, as appropriate to the form of the immunostimulatory combination) in an amount effective to increase the immune response to a particular antigen. For example, the TLR agonist can be administered in an amount from about 100 ng/kg to about 100 mg/kg. In many embodiments, the TLR agonist is administered in an amount from about 10 µg/kg to about 10 mg/kg. In some embodiments, the TLR agonist is administered in an amount from about 1 mg/kg to about 5 mg/kg. The particular amount of TLR agonist that constitutes an amount effective to increase the immune response to a particular antigen, however, depends to some extent upon certain factors including but not limited to the particular TLR agonist being administered; the particular antigen being administered and the amount thereof; the particular TNF/R agonist being administered and the amount thereof; the state of the immune system (e.g., suppressed, compromised, stimulated); the method and order of administration of the TLR agonist, the TNF/R agonist, and the antigen; the species to which the formulation is being administered; and the desired therapeutic result. Accordingly it is not practical to set forth generally the amount that constitutes an effective amount of the TLR agonist. Those of ordinary skill in the art, however, can readily determine the appropriate amount with due consideration of such factors.

Also, for example, the TNF/R agonist may be administered in an amount from about 100 ng/kg to about 100 mg/kg. In certain embodiments, the TNF/R agonist is administered in an amount from about 10 µg/kg to about 10 mg/kg. In some embodiments, the TNF/R agonist is administered in an amount from about 1 mg/kg to about 5 mg/kg. The particular amount of TNF/R agonist that constitutes an amount effective to increase the immune response to a particular antigen, however, depends to some extent upon certain factors including but not limited to the particular TNF/R agonist being administered; the particular TLR agonist being administered and the amount thereof; the particular antigen being administered and the amount thereof; the state of the immune system; the method and order of administration of the TLR agonist, the TNF/R agonist, and the antigen; the species to which the formulation is being administered; and the desired therapeutic result. Accordingly it is not practical to set forth generally the amount that constitutes an effective amount of the TNF/R agonist. Those of ordinary skill in the art, however, can readily determine the appropriate amount with due consideration of such factors.

In some embodiments, the immunostimulatory combination may further include an antigen. When present in the immunostimulatory combination, the antigen may be administered in an amount that, in combination with the other components of the combination, is effective to generate an immune response against the antigen. For example, the antigen can be administered in an amount from about 100 ng/kg to about 100 mg/kg. In many embodiments, the antigen may be administered in an amount from about 10 µg/kg to about 10 mg/kg. In some embodiments, the antigen may be administered in an amount from about 1 mg/kg to about 5 mg/kg. The particular amount of antigen that constitutes an amount effective to generate an immune response, however, depends to some extent upon certain factors such as, for example, the particular antigen being administered; the particular TLR agonist being administered and the amount thereof; the particular TNF/R agonist being administered and the amount thereof; the state of the immune system; the method and order of administration of the TLR agonist, the TNF/R agonist, and the antigen; the species to which the formulation is being administered; and the desired therapeutic result. Accordingly, it is not practical to set forth generally the amount that constitutes an effective amount of the antigen. Those of ordinary skill in the art, however, can readily determine the appropriate amount with due consideration of such factors.

When present, the antigen may be administered simultaneously or sequentially with any component of the immunostimulatory combination. Thus, the antigen may be administered alone or in a mixture with one or more adjuvants (including, e.g., a TLR agonist, a TNF/R agonist, or both). In some embodiments, an antigen may be administered simultaneously (e.g., in a mixture) with respect to one adjuvant, but sequentially with respect to one or more additional adjuvants.

Sequential co-administration of an antigen and other components of an immunostimulatory combination can include cases in which the antigen and at least one other component of the immunostimulatory combination are administered so that each is present at the treatment site at the same time, even though the antigen and the other component are not administered simultaneously. Sequential co-administration of the antigen and the other components of the immunostimulatory combination also can include cases in which the antigen or at least one of the other components of the immunostimulatory combination is cleared from a treatment site, but at least one cellular effect of the cleared antigen or other component (e.g., cytokine production, activation of a certain cell population, etc.) persists at the treatment site at least until one or more additional components of the combination are administered to the treatment site. Thus, it may be possible that an immunostimulatory combination of the invention can, in certain circumstances, include one or more components that never exist in a mixture with another component of the combination.

The antigen can be any material capable of raising a $T_H1$ immune response, which may include one or more of, for example, a $CD8^+$ T cell response, an NK T cell response, a $\gamma/\delta$ T cell response, or a $T_H1$ antibody response. Suitable antigens include but are not limited to peptides; polypeptides; lipids; glycolipids; polysaccharides; carbohydrates; polynucleotides; prions; live or inactivated bacteria, viruses or fungi; and bacterial, viral, fungal, protozoal, tumor-derived, or organism-derived antigens, toxins or toxoids.

Furthermore, it is contemplated that certain currently experimental antigens, especially materials such as recombinant proteins, glycoproteins, and peptides that do not raise a strong immune response, can be used in connection with adjuvant combinations of the invention. Exemplary experimental subunit antigens include those related to viral disease such as adenovirus, AIDS, chicken pox, cytomegalovirus, dengue, feline leukemia, fowl plague, hepatitis A, hepatitis B, HSV-1, HSV-2, hog cholera, influenza A, influenza B, Japanese encephalitis, measles, parainfluenza, rabies, respiratory syncytial virus, rotavirus, wart, and yellow fever.

In certain embodiments, the antigen may be a cancer antigen or a tumor antigen. The terms cancer antigen and tumor antigen are used interchangeably and refer to an antigen that is differentially expressed by cancer cells. Therefore, cancer antigens can be exploited to differentially target an immune response against cancer cells. Cancer antigens may thus potentially stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-C017-1A/GA733, Carcinoembryonic Antigen (CEA) and its antigenic epitopes CAP-1 and CAP-2, etv6, aml1, Prostate Specific Antigen (PSA) and its antigenic epitopes PSA-1, PSA-2, and PSA-3, prostate-specific membrane antigen (PSMA), T-cell receptor/CD3-ζ chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γcatenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, aml1, cyclophilin b), B cell lymphoma (Ig-idiotype), glioma (E-cadherin, α-catenin, β-catenin, γ-catenin, p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-CO17-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100$^{Pmel117}$), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

Immunostimulatory combinations of the invention that include an antigen may form a vaccine. Such vaccines can contain additional pharmaceutically acceptable ingredients, excipients, carriers, and the like well known to those skilled in the art.

Immunostimulatory combinations of the invention can be administered to animals, e.g., mammals (human and non-human), fowl, and the like according to conventional methods well known to those skilled in the art (e.g., orally, subcutaneously, nasally, topically).

The invention also provides therapeutic and/or prophylactic methods that include administering an immunostimulatory combination of the invention to a subject.

Unless a specific sequence of administration is provided, components of the immunostimulatory combination may be administered simultaneously with the antigen (together in admixture or separately, e.g., orally or by separate injection) or subsequent to administering one or more other components of the immunostimulatory combination. For example, a TLR agonist and a TNF/R agonist may be administered simultaneously with one another or sequentially with respect to each other. Also, when an antigen is present as a component of the immunostimulatory combination, it may be administered simultaneously with, or sequentially with respect to, any other component of the combination.

Components of the immunostimulatory combination can be administered simultaneously or sequentially in any order. When the components are administered simultaneously, they can be administered in a single formulation or in distinct formulations. When administered as distinct formulations, whether simultaneously or sequentially, the components may be administered at a single site or at separate sites. Also, when administered as distinct formulations, each formulation may be administered using a different route. Suitable routes of administration include but are not limited to transdermal or transmucosal absorption, injection (e.g., subcutaneous, intraperitoneal, intramuscular, intravenous, etc.), ingestion, inhalation, and the like. When administered sequentially, the time between administration of the components can be determined, at least in part, by certain factors such as, for example, the length of time a particular component persists, either systemically or at the administration site; or the length of time that the cellular effects of the component persist, either systemically or at the administration site, even after the component has been cleared.

Certain small molecule IRM compounds can induce biosynthesis of antiviral cytokines. Therefore, for certain embodiments that include a live viral antigen and a small molecule IRM compound as the TLR agonist component of the immunostimulatory combination, it may be desirable to administer the antigen prior to administering the IRM compound so that the viral infection can be established.

In one aspect, methods of the invention can include administering a vaccine including an immunostimulatory combination of the invention to induce a $T_H 1$ immune response in a subject. As noted above, certain small molecule IRMs, alone, may be useful as a vaccine adjuvant. An immunostimulatory combination that includes a TLR agonist (e.g., a small molecule IRM) and a TNF/R agonist can provide an even greater immune response than either an antigen alone, an antigen combined with a TLR agonist, or an antigen combined with a TNF/R agonist. In some cases, an immunostimulatory combination that includes a TLR agonist and a TNF/R agonist can synergistically increase an immune response compared to either a TLR agonist or TNF/R agonist.

Methods of the invention also include inducing an immune response from cells of the immune system regardless of whether the cells are in vivo or ex vivo. Thus, an immunostimulatory combination of the invention may be useful as a component of a therapeutic vaccine, a component of a prophylactic vaccine, or as an immunostimulatory factor used in ex vivo cell culture. When used to elicit an immune response ex vivo, the immune cells activated ex vivo may be reintroduced into a patient. Alternatively, factors secreted by the activated immune cells in the cell culture, (e.g., antibodies, cytokines, co-stimulatory factors, and the like) may be collected for investigative, prophylactic, or therapeutic uses.

Methods of the invention also include activating naive $CD8^+$ T cells in an antigen-specific manner in vivo. The population of activated antigen-specific $CD8^+$ T cells produced in response to co-administration of an antigen and an immunostimulatory combination—whether or not the antigen is explicitly a component of the immunostimulatory combination—may be divided into two functionally distinct sub-populations. One population of antigen-specific $CD8^+$ T cells includes effector T cells,—$CD8^+$ T cells actively engaged in providing a cell-mediated immune response. A second population of antigen-specific $CD8^+$ T cells includes memory T cells, $CD8^+$ T cells that are not themselves involved in providing an immune response, but can be readily induced to become antigen-specific effector cells upon a later contact with the same antigen. Activation of $CD8^+$ T cells according to the following method may induce expansion of antigen-specific $CD8^+$ effector T cells, generate antigen-specific $CD8^+$ memory T cells, or both.

An immunostimulatory combination that includes an antigen may be administered to a subject. After sufficient incubation in the subject, $CD8^+$ T cells will mature to antigen-specific $CD8^+$ effector T cells in response to the immunization. A greater percentage of $CD8^+$ effector T cells will be antigen-specific in subjects immunized with an immunostimulatory combination that includes a TLR agonist and a TNF/R agonist compared to subjects immunized with only antigen, antigen and a TNF/R agonist, or antigen and a TLR agonist. FIG. 1 shows flow cytometry data demonstrating the increased expansion of antigen-specific $CD8^+$ effector T cells when a subject is immunized with an immunostimulatory combination of the invention.

Generally, the incubation time between immunization and the generation of $CD8^+$ effector T cells is from about 4 days to about 12 days. In certain embodiments, $CD8^+$ effector T cells may be generated in about 5 days after immunization. In other embodiments, $CD8^+$ effector T cells may be generated in about 7 days after immunization.

Figure 2:
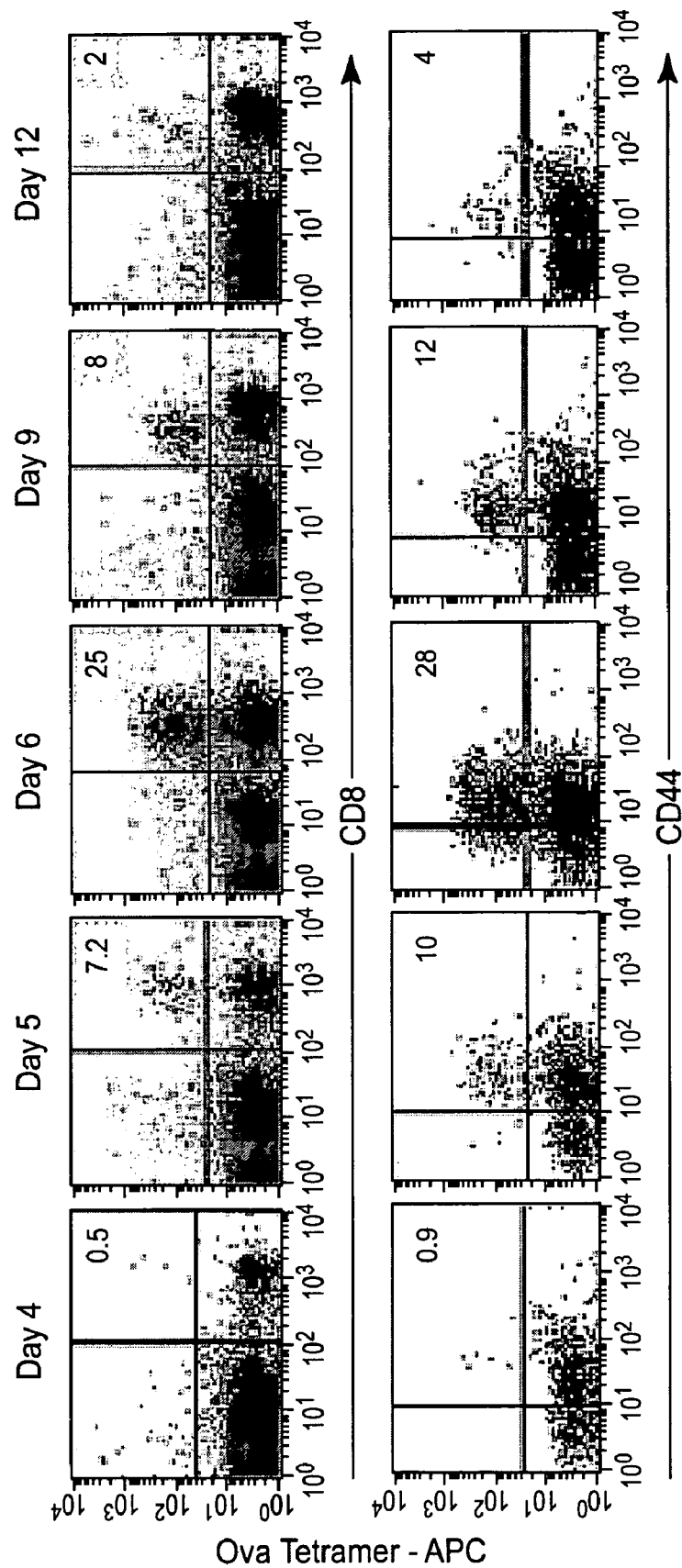
FIG. 2 shows flow cytometry data showing the results of Example 2.
Figure 3:
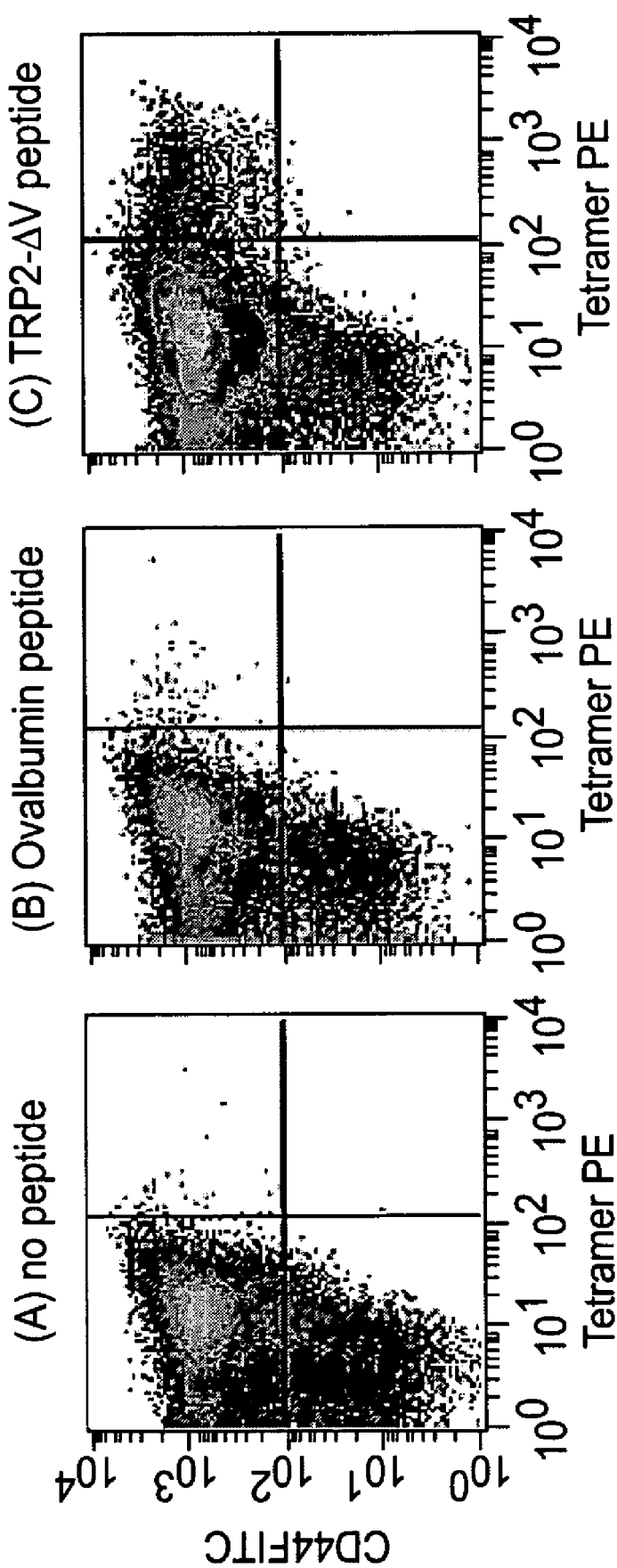
FIG. 3 shows flow cytometry data showing the results of Example 3.

If the antigen is a protein, it may not be necessary to administer the entire protein to the subject. FIG. 2 shows expansion kinetics of $CD8^+$ T cells in response to whole chicken ovalbumin, but FIG. 1 shows expansion of $CD8^+$ T cells using an eight amino acid peptide from chicken ovalbumin (SIINFEKL, SEQ ID NO:1). Similarly, FIG. 3 shows expansion of $CD8^+$ T cells in response to a TRP2-AV peptide (SIYDFFVWL, SEQ ID NO:2).

Thus, a method that includes administering to a subject an immunostimulatory combination of the invention may be used to elicit an antigen-specific response in $CD8^+$ cytotoxic T lymphocytes (CTLs) of the subject. Such a response may be directed against many conditions including, for example, tumors and virus-infected cell populations. In some embodiments of the invention, a vaccine of the invention may be administered prophylactically to provide a subject with a protective antigen-specific cell-mediated immunity directed against, for example, tumors and/or viral infections.

In an alternative embodiment, immunostimulatory combinations of the present invention may be used to develop antigen-specific $CD8^+$ memory T cells in vivo. The antigen-specific $CD8^+$ memory T cells may be capable of generating a secondary $T_H1$ immune response upon a second exposure to the antigen. $CD8^+$ effector T cells may be generated from the re-activated $CD8^+$ memory T cells in as little as 2 hours after re-exposure to the antigen. The second exposure to the antigen may be by immunization (i.e., a booster immunization) or natural exposure.

Figure 4:
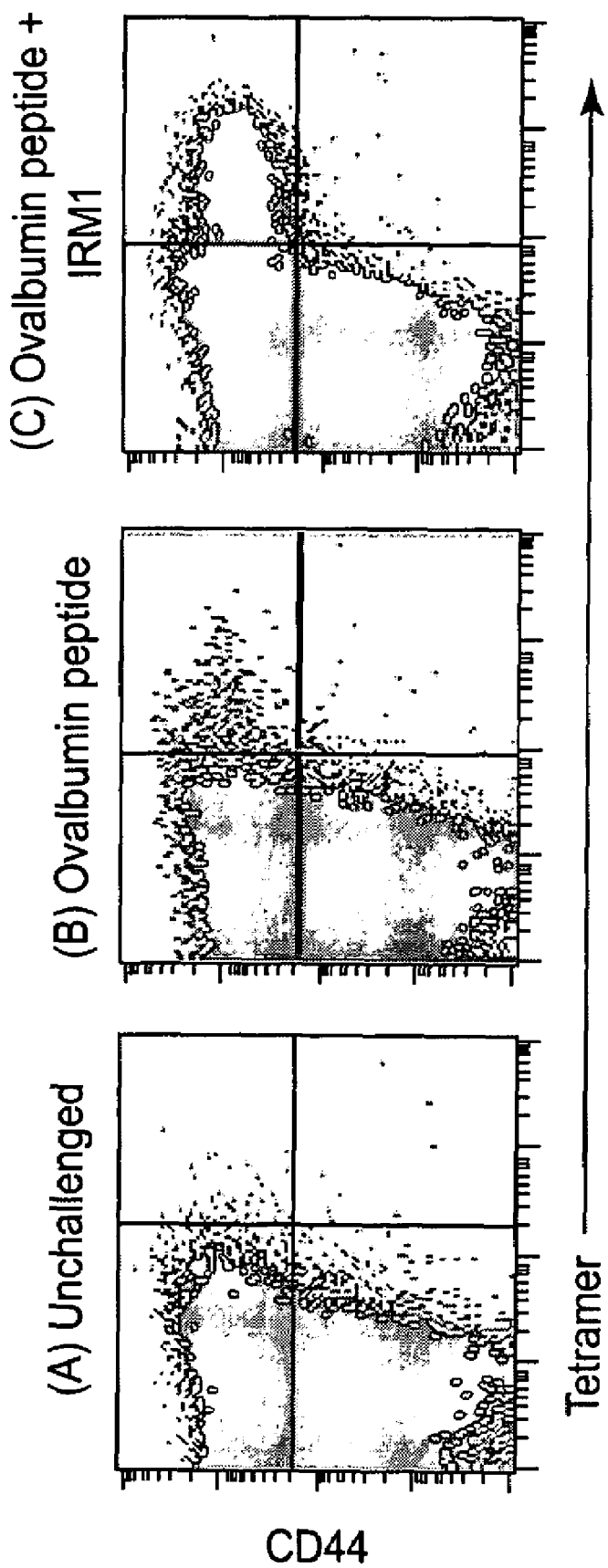
FIG. 4 shows flow cytometry data showing the results of Example 4.

FIG. 4 shows re-activation of antigen-specific $CD8^+$ memory T cells four weeks after being generated by co-administration of an antigen, a TLR agonist, and a TNF/R agonist. Re-activation of the $CD8^+$ memory T cells is induced by challenge with an antigen (panel B), but is even greater when challenged with co-administered antigen and TLR agonist (panel C). In certain cases, the antigen-specific cell-mediated immunologic memory described above may be supplemented by antigen-specific humoral immunologic memory provided by circulating antibodies resulting from a $T_H2$ immune response to one or more components of a vaccine.

An immunostimulatory combination of the invention can be used to therapeutically treat a condition treatable by a cell-mediated immune response. Such a combination can contain at least a therapeutically effective amount of a TLR agonist and a therapeutically effective amount of a TNF/R agonist. In many embodiments, a therapeutic combination can further include a therapeutically effective amount of an antigen.

A therapeutic combination can be provided in further combination with one or more pharmaceutically acceptable carriers. Because the TLR agonist, TNF/R agonist, and antigen (if present in the combination) may be co-administered sequentially, at different sites, and/or by different routes, a therapeutic combination may be provided in two or more formulations. When provided in two or more formulations, each formulation can include a carrier similar or different than the carrier or carriers included in the remaining formulations. Alternatively, the TLR agonist, TNF/R agonist, and antigen (if present in the combination) may be provided in a single formulation, which can include a single carrier or a combination of carriers.

Each component or mixture of components may be administered in any suitable conventional dosage form such as, for example, tablets, lozenges, parenteral formulations, syrups, creams, ointments, aerosol formulations, transdermal patches, transmucosal patches and the like.

Therapeutic immunostimulatory combinations can be administered as the single therapeutic agent in the treatment regimen. Alternatively, a therapeutic immunostimulatory combination of the invention may be administered in combination with another therapeutic combination of the invention, with one or more pharmaceutical compositions, or with other active agents such as antivirals, antibiotics, additional IRM compounds, etc.

Because of their ability to induce the $T_H1$ immune response and generate a pool of $CD8^+$ effector T cells, certain immunostimulatory combinations of the invention can be particularly useful for treating viral diseases and tumors. This immunomodulating activity suggests that immunostimulatory combinations and vaccines of the invention are useful in treating conditions such as, but not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picomavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, or Bordetella;

(c) other infectious diseases, such chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection; and (d) neoplastic diseases, such as, for example, intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers (e.g., cancers identified above); and (e) $T_H2$-mediated, atopic, and autoimmune diseases, such as atopic dermatitis or eczema, eosinophilia, asthma, allergy, allergic rhinitis, systemic lupus erythematosus, essential thrombocythaemia, multiple sclerosis, Ommen's syndrome, discoid lupus, alopecia areata, inhibition of keloid formation and other types of scarring, and enhancing would healing, including chronic wounds.

Some embodiments of the immunostimulatory combinations of the invention also may be useful as a vaccine adjuvant for use in conjunction with any material that raises either humoral and/or cell mediated immune response, such as, for example, live viral, bacterial, or parasitic antigens; inactivated viral, tumor-derived, protozoal, organism-derived, fungal, or bacterial antigens, toxoids, toxins; self-antigens; polysaccharides; proteins; glycoproteins; peptides; cellular vaccines; DNA vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Immunostimulatory combinations of the invention may also be particularly helpful in individuals having compromised immune function. For example, IRM, compounds may be used for treating the opportunistic infections and tumors that occur after suppression of cell mediated immunity in, for example, transplant patients, cancer patients and HIV patients.

The invention also provides a method of treating a viral infection in an animal and a method of treating a neoplastic disease in an animal comprising administering a therapeutically effective amount of an immunostimulatory combination of the invention to the animal. A therapeutically effective amount to treat or inhibit a viral infection is an amount that will cause a reduction in one or more of the manifestations of viral infection, such as viral lesions, viral load, rate of virus production, and mortality as compared to untreated control animals. A therapeutically effective amount of a combination to treat a neoplastic condition is an amount that will cause, for example, a reduction in tumor size, a reduction in the number of tumor foci, or slow the growth of a tumor, as compared to untreated animals.

Figure 5:
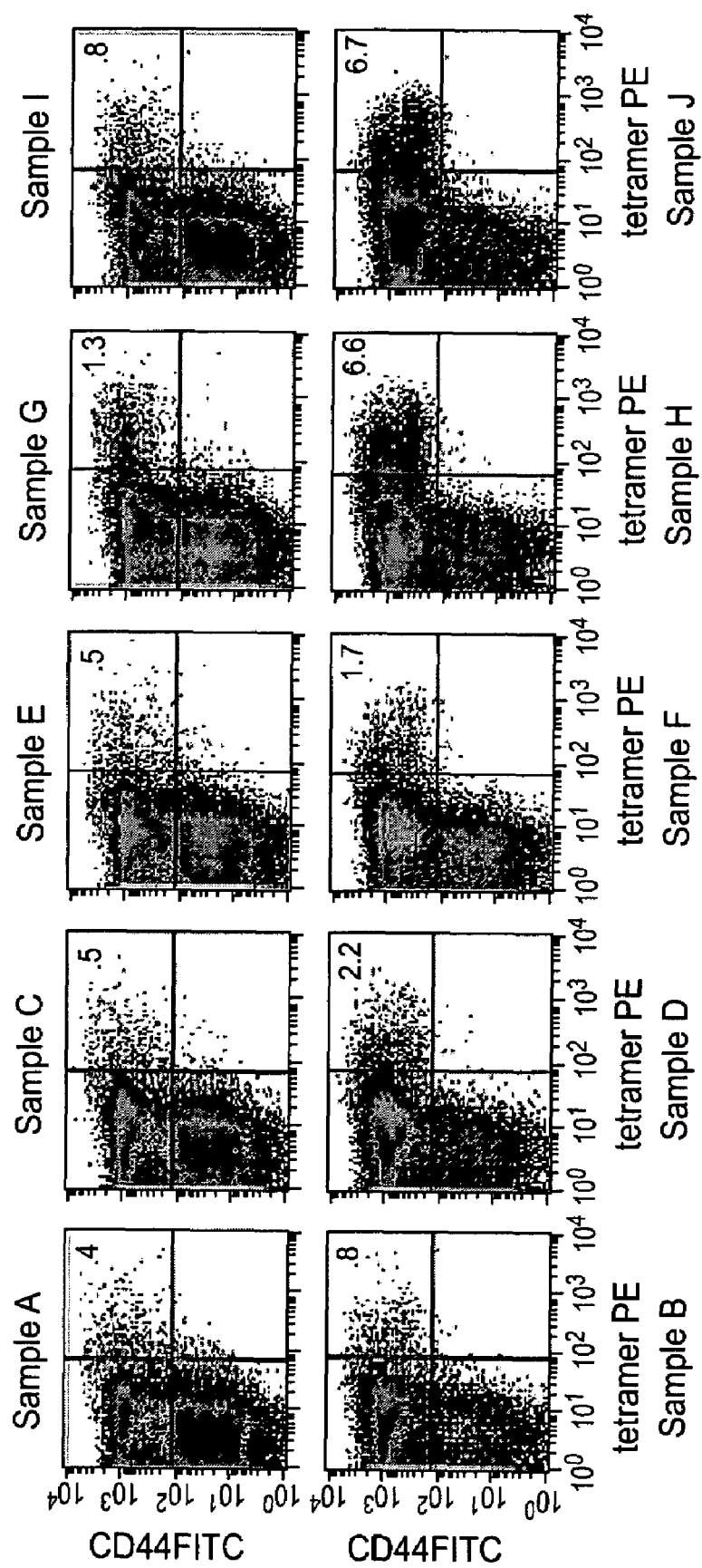
FIG. 5 shows flow cytometry data showing the results of Example 5.

In one particular embodiment, an immunostimulatory combination of the invention may be used to inhibit tumor growth in vivo. Subjects having tumor cells expressing a particular antigen may be immunized with a therapeutic combination that contains a TLR agonist, a TNF/R agonist, and, optionally, the antigen. In some embodiments, the therapy can include an initial immunization and a second booster immunization. Tumors taken from subjects immunized with a therapeutic combination of the invention were generally smaller than the tumors harvested from either (a) non-immunized subjects, or (b) subjects immunized with only the antigen (FIGS. 5 and 6).

Figure 6:
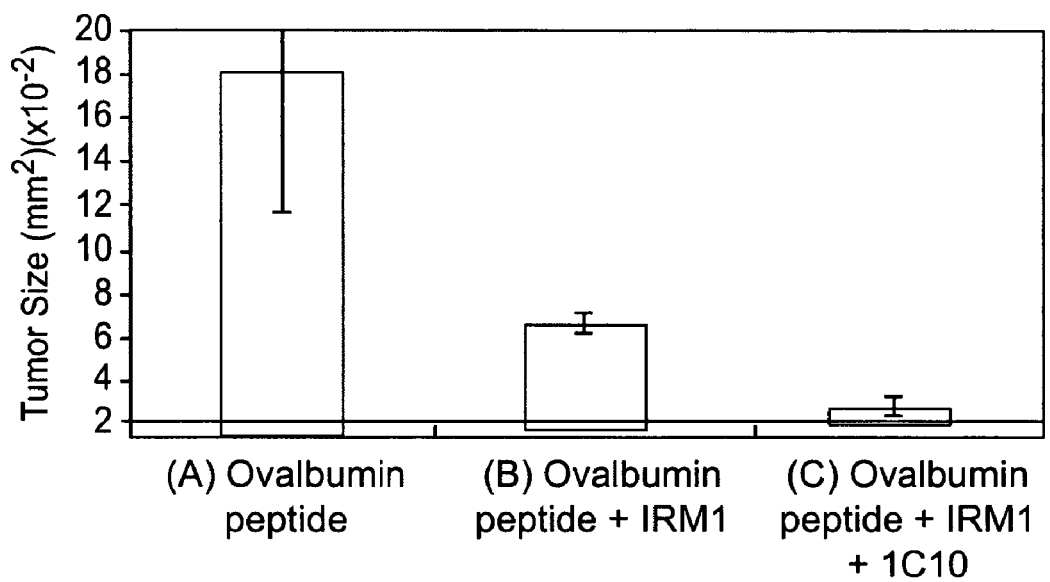
FIG. 6 is a bar graph showing the results of Example 6.

FIG. 6 compares tumor size in mice challenged with melanoma cells that express ovalbumin as a tumor antigen. Seven days after challenge with the melanoma cells, the mice were immunized with either (a) ovalbumin peptide, (b) ovalbumin peptide and TLR agonist, or (c) ovalbumin peptide, TLR agonist, and TFNR agonist. On day 21 (14 days after immunization), tumors were removed and measured. The antigen/TLR agonist/TFNR agonist combination provided superior protection against tumor growth compared to the protection provided by immunization with the antigen or an antigen/TLR agonist combination.

Figure 7:
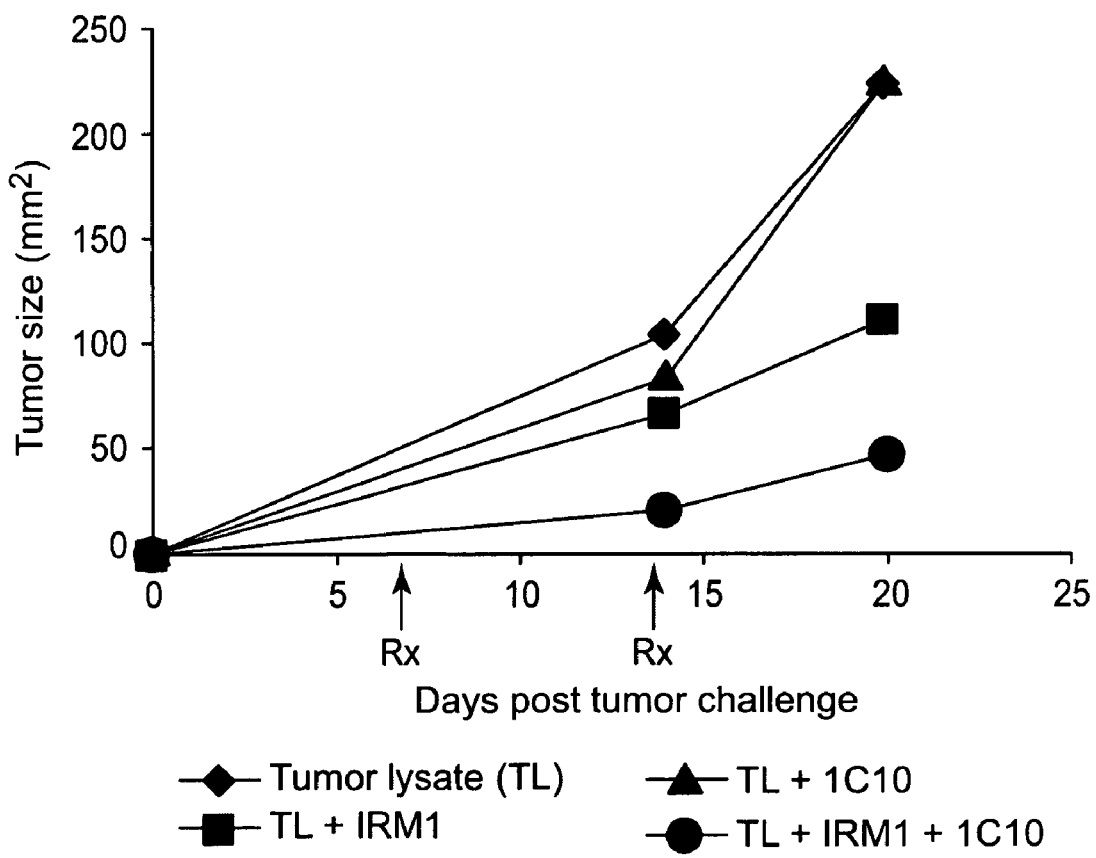
FIG. 7 is a line graph showing the results of Example 7.

FIG. 7 compares tumor size in mice challenged with melanoma cells that express ovalbumin as a tumor antigen, in which (a) the mice received two immunizations against the tumor, and (b) the antigen component of the immunization included tumor cell lysate rather than ovalbumin peptide. FIG. 7 shows that immunization with a combination of TNF/R agonist and antigen provided little or no protection against tumor growth compared to mice immunized with only antigen. Again, the antigen/TLR agonist/TFNR agonist combination provided superior protection against tumor growth compared to the protection provided by immunization with the antigen or an antigen/TLR agonist combination.

Figure 10A:
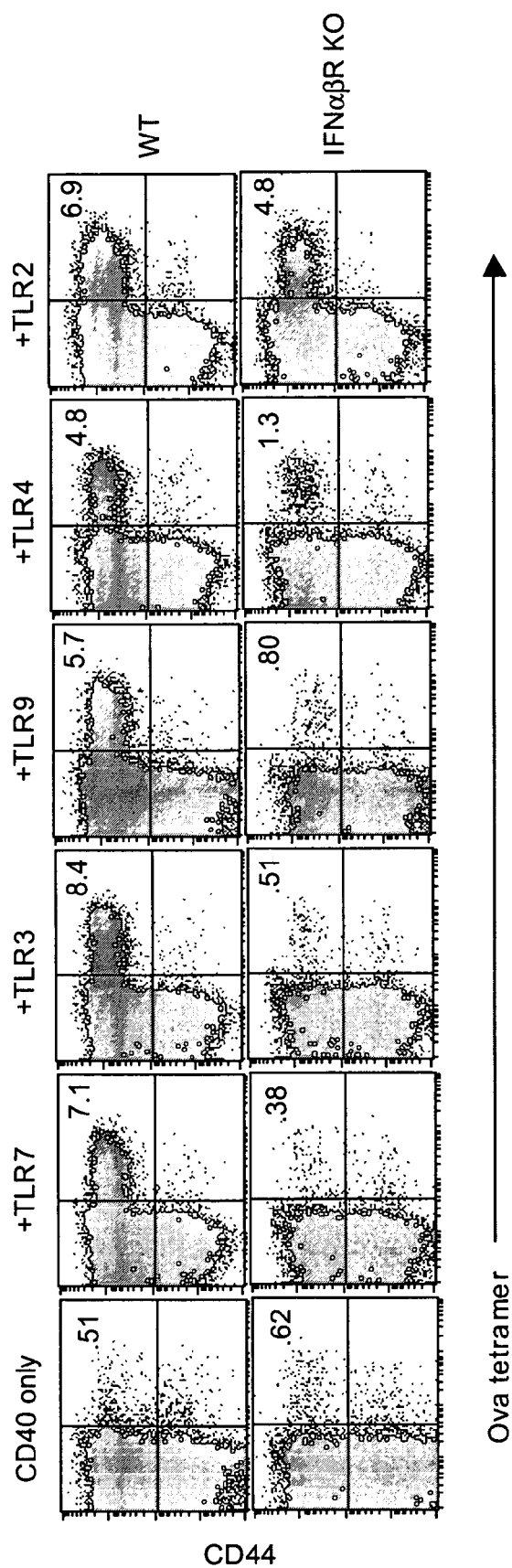
FIG. 10A shows flow cytometry data showing the results of Example 10.
Figure 10B:
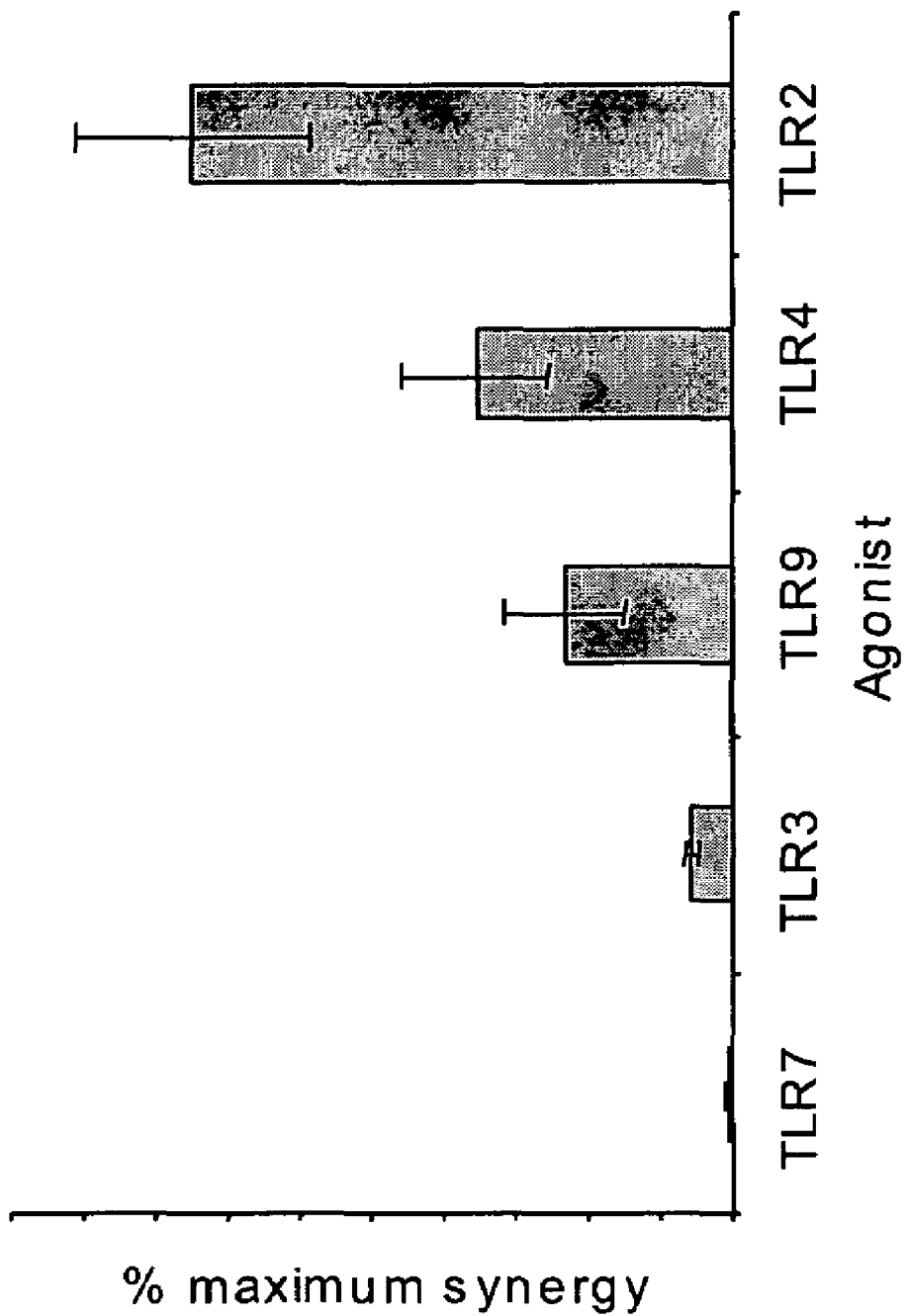
FIG. 10B is a bar graph showing the results of Example 10.

In some cases, the extent to which the synergistic nature of an immune response to an immunostimulatory combination depends upon Type I interferon correlates with the Type I interferon stimulation typically observed by activating the TLR that is activated by the TLR agonist of the combination. FIG. 10 shows that the synergistic nature of an immune response to an immunostimulatory combination that includes, as the TLR agonist, an agonist of a TLR that typically induces Type I interferons (e.g., TLR7, TLR3, TLR9, and TLR4) can be significantly reduced in mice lacking receptors for Type I interferons. Thus, the synergistic immune response to such immunostimulatory combinations is at least partially dependent upon Type I interferon. FIG. 10 also shows, however, that the synergistic immune response generated with an immunostimulatory combination that includes an agonist of a TLR that typically induces very little or no Type I interferon synthesis (MALP-2, a TLR2/6 agonist) is independent of Type I interferon.

Figure 11:
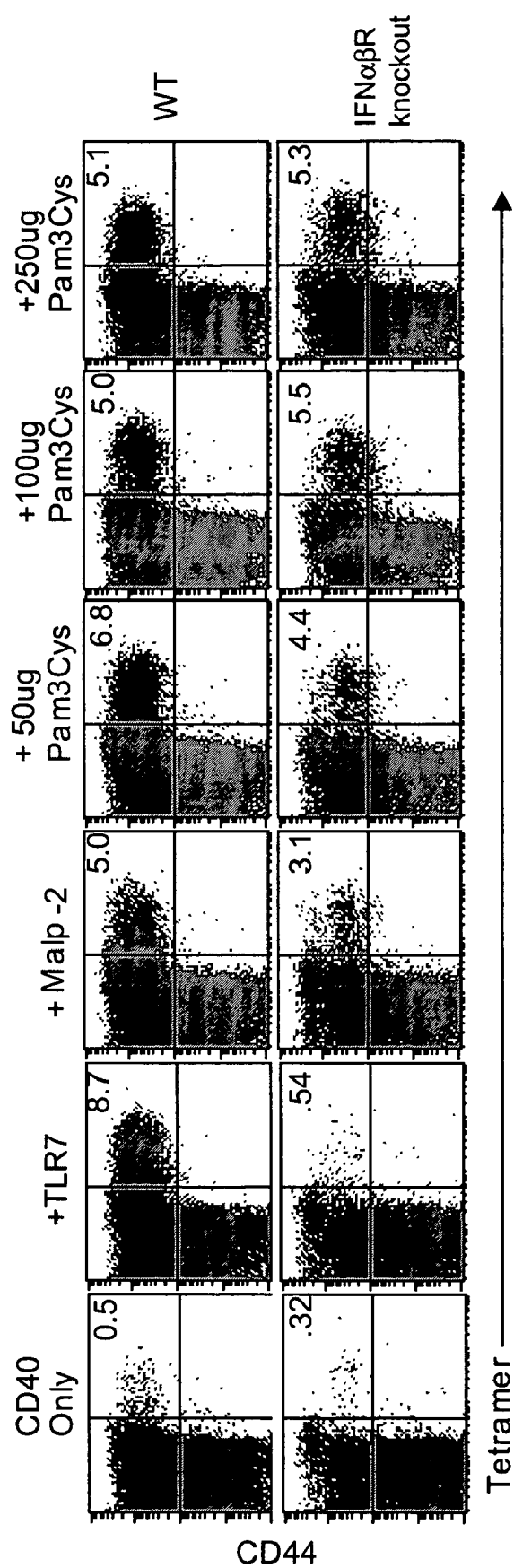
FIG. 11 shows flow cytometry data showing the results of Example 11.

Furthermore, FIG. 11 shows that the interferon-independent synergistic immune response induced by an immunostimulatory combination that includes MALP-2 can be induced using other TLR2 agonists. For example, the TLR2 agonist Pam3cys also can induce a synergistic immune response in IFNαβ receptor knock out mice (i.e., mice unable to process interferon-dependent cellular signal).

Thus, it may be possible, using the methods of the invention, to tailor an immunostimulatory combination according to a desired level of Type I interferon induction, a desired Type I interferon dependency of the immune response, or both. For example, an immunostimulatory combination that includes a TLR7 agonist may be desirable when a high level of interferon induction and/or an immune response that is Type I interferon dependent is sought such as, for example, for providing therapeutic or prophylactic treatment against a viral infection. Alternatively, for cases in which a synergistic immune response is sought without inducing Type I interferon production, an immunostimulatory combination may include a TLR2 agonist such as, for example, for providing therapeutic or prophylactic treatment against a subcutaneous bacterial infection or a parasitic infection.

Treatments according to the present invention may include one or more than one immunization. When the treatment includes more than one immunization, the treatment can include any suitable number of immunizations administered at any suitable frequency. The number and frequency of immunizations in a treatment regimen depend at least in part upon one or more factors including but not limited to the condition being treated and the stage thereof, the state of the subject's immune system, the particular TLR agonist being administered and the amount thereof, the particular TNF/R agonist being administered and the amount thereof, and the particular antigen being administered (if present) and the amount thereof.

In some embodiments, therapeutic combinations of the invention may not require an antigen component. For certain conditions (e.g., B cell lymphoma or chronic bacterial or viral infections), effective treatment may be obtained using an immunostimulatory combination that does not include an antigen. Such conditions may be treatable in this way because, for example, the condition may provide a sufficient quantity or variety of condition-specific antigens to generate a cell-mediated immune response capable of treating the condition.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

Unless otherwise indicated, mice used in the following examples are C57BL6 mice, available from Charles River Laboratories, Inc., Wilmington, Mass.

TLR agonists used in the Examples that follow are identified in Table 1.

TABLE 1

| TLR agonist | Compound Name | Reference |
|---|---|---|
| IRM1 | 4-amino-α,α,2-trimethyl-1H-imidazo[4,5-c]quinolin-1-ethanol | U.S. Pat. No. 5,266,575 Example C1 |
| IRM2 | N-(2-{2-[4-amino-2-(2-methoxyethyl)-1H-imidazo[4,5-c]quinolin-1-yl]ethoxy}ethyl)-N-methylmorpholine-4-carboxamide | WO 02/46191 Example 6 |
| IRM3 | 1-(2-amino-2-methylpropyl)-2-(ethoxymethyl)-1H-imidazo[4,5-c]quinolin-4-amine | U.S. Pat. No. 6,069,149[#] |
| IRM4 | N-[4-(4-amino-2-ethyl-1H-imidazo[4,5-c]quinolin-1-yl)butyl]-methanesulfonamide | U.S. Pat. No. 6,331,539[#] |
| IRM5 | N-[4-(4-amino-2-propyl-1H-imidazo[4,5-c]quinolin-1-yl)butyl]-methanesulfonamide | U.S. Pat. No. 6,331,539[#] |

[#]This compound is not specifically exemplified but can be readily prepared using the synthetic methods disclosed in the cited reference.

Ovalbumin peptide (SIINFEKL, SEQ ID NO:1) and TRP2-ΔV peptide (SIYDFFVWL, SEQ ID NO:2) were obtained from American Peptide Co., Sunnyvale, Calif.

MHC tetrameric reagent was prepared using a eukaryotic (Baculovirus) expression system as follows/described in Kedl et al., JEM 192(8): 1105-1113 (2000).

Example 1

2-5 Mice were immunized intravenously with (A) 100 μg ovalbumin peptide, (B) 100 μg ovalbumin peptide+100 μg anti-CD40 antibody (IC10), (C) 100 μg ovalbumin peptide+200 μg IRM1, or (D) 100 μg ovalbumin peptide+100 μg IC10 anti-CD40 antibody+200 μg IRMI. At five days after the immunizations, the spleens were removed from the mice and homogenized. The homogenized cell suspension was stained with a major histocompatibility complex (MHC) tetrameric reagent for detecting ovalbumin-specific T cells (Kedl et al., JEM 192(8): 1105-1113 (2000)), a CD8 stain (BD Biosciences Pharmingen, San Diego, Calif.), and a CD44 stain (BD Biosciences Pharmingen, San Diego, Calif.). When subjected to flow cytometry, ovalbumin-specific CD8$^+$ T cells are shown in the upper right quadrant of the dot plots shown in FIG. 1. Expansion of the ovalbumin-specific CD8$^+$ T cell population after stimulation with the combination of the anti-CD40 antibody and IRM was greater than the expansion of the ovalbumin-specific CD8$^+$ T cell populations after stimulation with either the anti-CD40 antibody or IRM alone.

Example 2

Mice were intraperitoneally injected with 5 mg ovalbumin (Sigma Chemical Co., St. Louis, Mo.), 50 µg FGK4.5 anti-CD40 antibody, and 220 µg IRM1. Mice were sacrificed on each of days four, five, six, nine, and twelve. The spleens were removed from the sacrificed mice and homogenized. The homogenized cell suspensions were stained and analyzed as described in Example 1. When subjected to flow cytometry, ovalbumin-specific $CD8^+$ T cells (top) and ovalbumin-specific $CD8^+/CD44+$ T cells (bottom) were identified and are shown in the upper right quadrant of each dot plot. The numbers in the upper right quadrant indicate the percentage of cells in that quadrant. These data shown that the synergistic effect on $CD8^+$ T cell expansion observed in Example 1 also is observed with (a) a different CD40 agonist, and (b) full-sized ovalbumin protein as the antigen.

Example 3

Mice were immunized intravenously with 100 µg FGK4.5 anti-CD40 antibody+200 µg IRM1 and either (A) no TRP2-ΔV peptide. At five days after the immunizations, the spleens were removed from the mice and homogenized. The homogenized cell suspension was stained as in Example 1, except that the MHC tetramer reagent was prepared for detecting TRP2-ΔV-specific T cells. When subjected to flow cytometry, TRP2-ΔV-specific $CD8^+$ T cells are shown in the upper right quadrant of the dot plots shown in FIG. 3. The numbers in the upper right quadrant indicate the percentage of cells in that quadrant. The data show synergistic expansion of antigen-specific $CD8^+$ T cells after stimulation with the combination of the anti-CD40 antibody and an IRM with yet another antigen.

Example 4

Mice were immunized intravenously on day 0 with 100 µg ovalbumin peptide+200 µg IRM1+100 µg of IC10 anti-CD40 antibody. On day 28, the mice were either (A) left unchallenged, (B) challenged intravenously with 100 µg ovalbumin peptide, or (C) challenged intravenously with 100 µg ovalbumin peptide+200 µg IRM1. On day 33, the mice were sacrificed, the spleens removed and spleen cells homogenized. The homogenized cells were stained and analyzed as described in Example 1. The data are shown in FIG. 4. The synergistic expansion of $CD8^+$ T cells that occurs as a result of immunizing with an antigen, a CD40 agonist, and an TLR agonist (shown in Example 1) generates a pool of long-lived $CD8^+$ memory T cells that can be reactivated by treatment with IRM and the antigen, shown in (C).

Example 5

Mice were immunized intravenously as indicated in Table 2. At five days, the mice were sacrificed, spleens harvested, and the cells homogenized, stained, and analyzed as in Example 1. The data are shown in FIG. 5. The numbers in the upper right quadrant indicate the percentage of cells in that quadrant.

TABLE 2

Immunization combinations for Example 5

| Sample | 3 mg ovalbumin | 100 µg CD40 agonist | Stimulus |
|---|---|---|---|
| A | + | + | none |
| B | + | − | none |
| C | + | + | 50 µg CpG |
| D | + | − | 50 µg CpG |
| E | + | + | 30 µg LPS |
| F | + | − | 30 µg LPS |
| G | + | + | 50 µg PolyIC |
| H | + | − | 50 µg PolyIC |
| I | + | + | 200 µg IRM1 |
| J | + | − | 200 µg IRM1 |

Example 6

Mice were challenged intradermally on day 0 with $1\times10^5$ melanoma B16ova tumor cells in PBS (Kedl et al. PNAS 98(19): 10811-10816). On day 7, the mice were immunized with either (A) 100 µg ovalbumin peptide, (B) 100 µg ovalbumin peptide+200 µg IRM1, or (C) 100 µg ovalbumin peptide+200 µg IRM1+100 µg IC10 anti-CD40 antibody. On day 21, the mice were sacrificed and the tumors were measured in two dimensions by caliper. Data are shown in FIG. 6. Immunization with antigen, IRM and CD40 agonist resulted in slower tumor growth than immunization with IRM alone.

Mice also were challenged as described above, and immunized as described above except that IRM2 was substituted for IRM1. The results observed using IRM2 in place of IRM1 were similar to the results observed using IRM1.

Example 7

Mice were challenged with tumor on day 0 as in example 6. 5 mice each were immunized on days 7 with $1\times10^6$ cell equivalents (CE) (A) tumor lysate, (B)$1\times10^6$ CE tumor lysate+200 µg IRM1, (C) $1\times10^6$ CE tumor lysate+100 µg FGK4.5 anti-CD40 antibody, or (D) $1\times10^6$ CE tumor lysate+200 µg IRM1+100 µg FGK4.5 anti-CD40 antibody. Tumor sizes were measured on the mice by caliper on days 14 and 20. The data are shown in FIG. 7. Immunization with the combination of IRM and anti-CD40 agonists resulted in slower tumor growth than immunization with IRM alone or CD40 agonist alone.

Example 8

Figure 8:
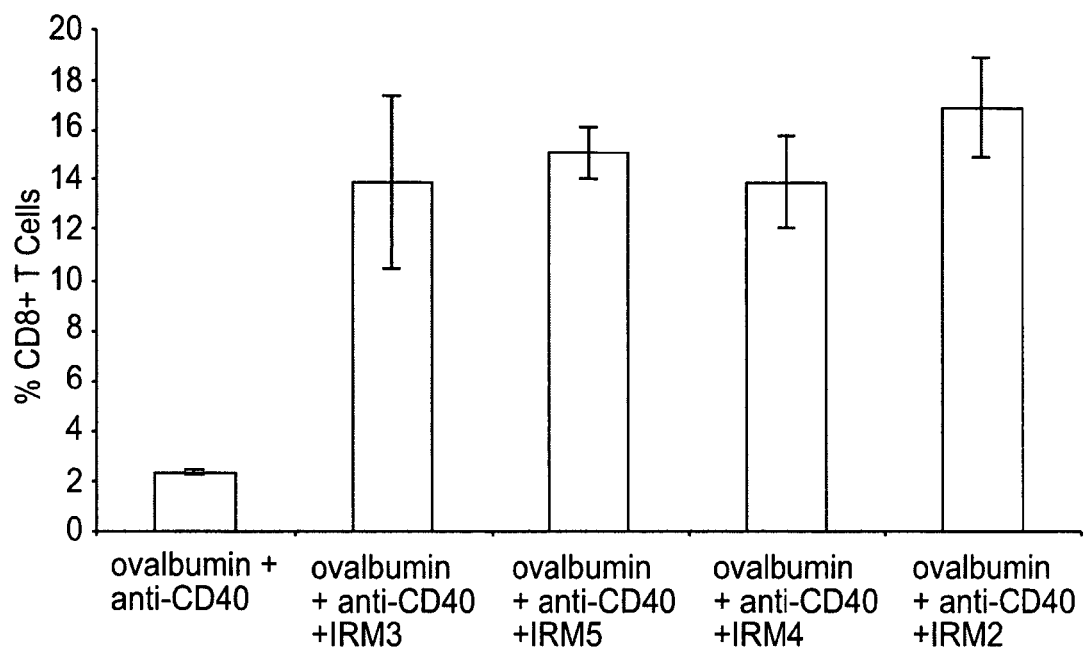
FIG. 8 is a bar graph showing the results of Example 8.

Mice were intraperitoneally injected on day 0 with 500 µg ovalbumin, 50 µg CD40 agonist (FGK4.5), and either 500 µg IRM3, 200 µg IRM4, 800 µg IRM5, 800 µg IRM2, or no IRM (control). On day 6, the mice were sacrificed and spleen cells were harvested and analyzed as described in Example 2. FIG. 8 shows the average percentage of $CD8^+$ T cells observed in each group of mice (n=3 for each group). Synergistic expansion of $CD8^+$ T cells is demonstrated using CD40 agonist in combination with different IRM compounds.

Example 9

Figure 9:
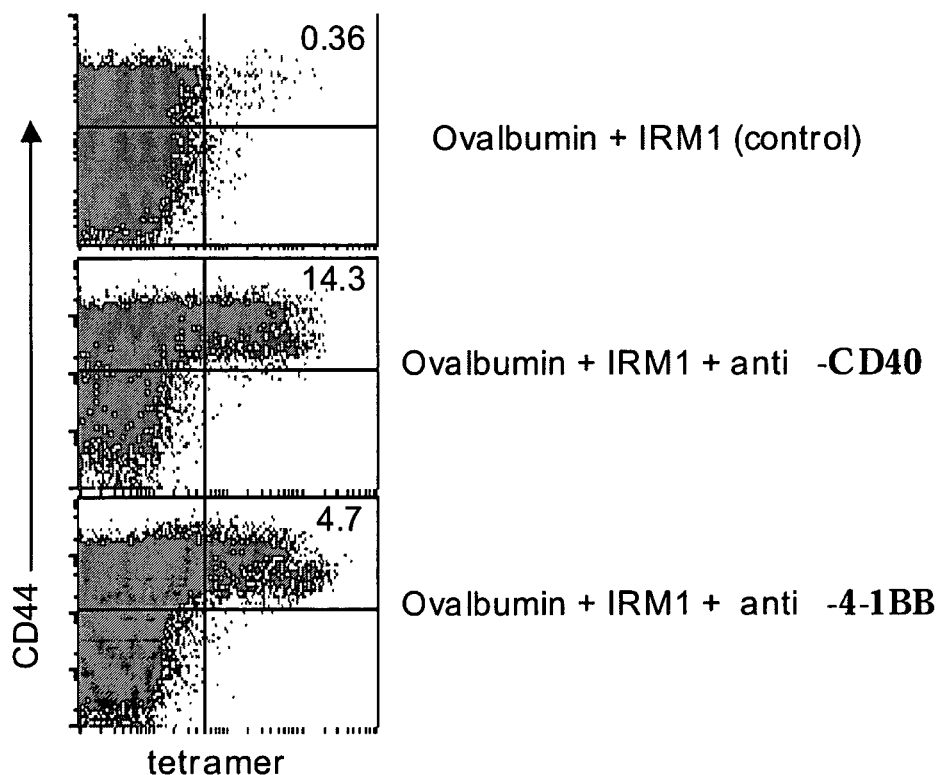
FIG. 9 shows flow cytometry data showing the results of Example 9.

Mice were immunized on day 0 with 1 mg ovalbumin, 200 µg IRM1, and either 200 µg CD40 ligand (FGK4.5), 200 µg 4-1BB ligand (anti-mouse 4-1BB antibody, clone 17B3, eBioscience, San Diego, Calif.), or no TNF/R agonist (control). On day 6, the mice were sacrificed and spleen cells were harvested and analyzed as described in Example 2. The results are shown in FIG. 9. Synergistic expansion of CD8+ T cells is demonstrated using IRM1 in combination with different TNF/R agonists.

Example 10

On day 0, a set of wild-type mice (B6/129 µl, Taconic, Germantown, N.Y.) and a set of IFNαβ receptor knockout mice (National Jewish Medical and Research Center, Denver Colo.) were injected intraperitoneally with 100 µg SIINFEKL peptide, 50 µg FGK45 (CD40 agonist), and either (a) nothing (CD40 only), (b) 100 µg IRM1 (+TLR7), (c) 50 µg poly IC (+TLR3), 100 µg CpG (+TLR9), 30 µg LPS (+TLR4), or 25 µg MALP-2 (+TLR2). On day 6, the mice were sacrificed and spleen cells were harvested and analyzed as described in Example 2.

as described in Example 2. The results are shown in FIG. 11. The interferon-independent synergistic immune response observed when an immunostimulatory combination that includes MALP-2, a TLR2/6 agonist, is also observed using an immunostimulatory combination that includes Pam3cys, a TLR2 agonist.

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

```
SEQUENCE LISTING

<160> NUMBER OF SEQ ID NOS: 2

<210> SEQ ID NO 1
<211> LENGTH: 8
<212> TYPE: PRT
<213> ORGANISM: Artificial
<220> FEATURE:
<223> OTHER INFORMATION: CD40 agonist peptide

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Artificial
<220> FEATURE:
<223> OTHER INFORMATION: CD40 agonist peptide

<400> SEQUENCE: 2

Ser Ile Tyr Asp Phe Phe Val Trp Leu
1               5
```

FIG. 10 shows the percentage of tetramer+T cells generated in wild-type and IFN knockout mice after immunization of mice with immunostimulatory combinations and, therefore, the IFN dependency of the synergistic immune response when induce by immunostimulatory combinations that include agonists of various TLRs.

Example 11

A set of wild-type mice (B6/129 F1, Taconic, Germantown, N.Y.) and a set of IFNαβ receptor knockout mice (National Jewish Medical and Research Center, Denver Colo.) were injected intraperitoneally with 50 µg FGK45 (CD40 agonist) on day 0. Four hours later, the mice were injected intravenously with 100 µg SIINFEKL alone, or with either 100 µg IRM1 (TLR7 agonist), 25 µg MALP-2, 50 µg Pam3cys (Alexis Biochemicals, Corp., San Diego, Calif.), 100 µg Pam3cys, or 250 µg Pam3cys. On day 6, the mice were sacrificed and spleen cells were harvested and analyzed

What is claimed is:

1. An immunostimulatory composition suitable for administration to a human subject in need of immunotherapy comprising:
   (i) at least one Toll-Like Receptor (TLR) agonist which is selected from the group consisting of TLR1, TLR2, TLR3, TLR4, TLR5, TLR6, TLR7, and TLR8 agonists; and
   (ii) at least one CD40 agonist that directly binds CD40; and
   (iii) a pharmaceutically acceptable carrier,
   wherein (i) and (ii) are each comprised in an amount such that, in combination with the other, are effective to produce a synergistic increase in a human subject in an immune response to an antigen upon administration to a human subject in need of immunotherapy.

2. An immunostimulatory composition suitable for administration to a human subject in need of immunotherapy comprising:

(i) at least one Toll-Like Receptor (TLR) agonist;
(ii) at least one 4-1BB agonist that directly binds 4-1BB; and
(iii) a pharmaceutically acceptable carrier,
wherein (i) and (ii) are each comprised in an amount such that, in combination with the other, are effective to produce a synergistic increase in a human subject in an immune response to an antigen upon administration to a human subject in need of immunotherapy.

3. The immunostimulatory composition of claim 2 wherein the at least one Toll-Like Receptor (TLR) agonist is selected from the group consisting of TLR1, TLR2, TLR3, TLR4, TLR5, TLR6, TLR7, TLR8 and TLR9 agonists.

4. The immunostimulatory composition of claim 1 wherein the at least one CD40 agonist comprises an agonistic anti-CD40 antibody or an agonistic anti-CD40 antibody fragment.

5. The immunostimulatory composition of claim 1 wherein the (ii) at least one CD40 agonist comprises a CD40 ligand (CD40L) polypeptide or a CD40L polypeptide fragment.

6. The immunostimulatory composition of claim 1 wherein the (ii) at least one 4-1BB agonist comprises an anti-4-1BB antibody or an anti-4-1BB antibody fragment.

7. The immunostimulatory composition of claim 2 wherein the at least one 4-1BB agonist comprises a 4-1BB ligand polypeptide or a 4-1BB ligand polypeptide fragment.

8. The immunostimulatory composition of claim 1 wherein the at least one TLR agonist comprises an immune response modifier (IRM) compound or an agonist of TLR2.

9. The immunostimulatory composition of claim 2 wherein the at least one TLR agonist comprises an immune response modifier (IRM) compound or an agonist of TLR2.

10. The immunostimulatory composition of claim 1 wherein the at least one TLR agonist comprises an IRM compound, MALP-2, Pam3cys, LPS, polyIC or a combination of the foregoing.

11. The immunostimulatory composition of claim 2 wherein the at least one TLR agonist comprises an IRM compound, MALP-2, Pam3cys, LPS, polyIC, CpG or a combination of the foregoing.

12. The immunostimulatory composition of claim 1 wherein the at least one TLR agonist comprises an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

13. The immunostimulatory composition of claim 2 wherein the at least one TLR agonist comprises an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

14. The immunostimulatory composition of claim 1 wherein the at least one CD40 agonist comprises an anti-CD40 agonistic antibody.

15. The immunostimulatory composition of claim 1 which is suitable for administration to a human subject in need of immunotherapy by a route selected from the group consisting of oral, nasal, topical, and injection.

16. The immunostimulatory composition of claim 2 which is suitable for administration to a human subject in need of immunotherapy by a route selected from the group consisting of oral, nasal, topical, and injection.

17. The immunostimulatory composition of claim 1 which is suitable for injection to a human subject in need of immunotherapy.

18. The immunostimulatory composition of claim 2 which is suitable for injection to a human subject in need of immunotherapy.

19. The immunostimulatory composition of claim 15 wherein injection is selected from the group consisting of subcutaneous, intravenous, intraperitoneal, intramuscular and intravenous.

20. The immunostimulatory composition of claim 16 wherein injection is selected from the group consisting of subcutaneous, intravenous, intraperitoneal, intramuscular and intravenous.

21. The immunostimulatory composition of claim 2 wherein the at least one TLR agonist is a TLR9 agonist.

22. The immunostimulatory composition of claim 21 wherein the TLR agonist comprises a CpG compound.

23. A vaccine composition suitable for administration to a human subject in need thereof comprising:
(i) at least one TLR agonist which is selected from the group consisting of TLR 1, TLR2, TLR3, TLR4, TLR5, TLR6, TLR7, and TLR8 agonists;
(ii) at least one CD40 agonist that directly binds CD40;
(iii) at least one antigen; and
(iv) at least one pharmaceutically acceptable carrier;
wherein (i) and (ii) are each comprised in an amount that, in combination with the other, are effective for inducing a synergistic immune response to the (iii) antigen in a human subject upon administration of the vaccine.

24. A vaccine composition suitable for administration to a human subject in need thereof comprising:
(i) at least one TLR agonist;
(ii) at least one 4-1BB agonist that directly binds 4-1BB;
(iii) at least one antigen; and
(iv) at least one pharmaceutically acceptable carrier;
wherein (i) and (ii) are each comprised in an amount that, in combination with the other, are effective for inducing a synergistic immune response to the (iii) antigen in a human subject upon administration of the vaccine.

25. The vaccine composition of claim 24 wherein the (i) at least one TLR agonist is selected from the group consisting of TLR1, TLR2, TLR3, TLR4, TLR5, TLR6, TLR7, TLR8 and TLR9 agonists.

26. The vaccine composition of claim 23 wherein the at least one CD40 agonist comprises an agonistic anti-CD40 antibody or an agonistic anti-CD40 antibody fragment.

27. The vaccine composition of claim 23 wherein the (ii) at least one CD40 agonist comprises a CD40 ligand (CD40L) polypeptide or a CD40L polypeptide fragment.

28. The immunostimulatory composition of claim 24 wherein the (ii) at least one 4-1BB agonist comprises an agonistic anti-4-1BB antibody or an agonistic anti-4-1BB antibody fragment.

29. The immunostimulatory composition of claim 24 wherein the at least one 4-1BB agonist comprises a 4-1BB ligand polypeptide or a 4-1BB ligand polypeptide fragment.

30. The vaccine composition of claim 23 wherein the at least one TLR agonist comprises an immune response modifier (IRM) compound or an agonist of TLR2.

31. The vaccine composition of claim 24 wherein the at least one TLR agonist comprises an immune response modifier (IRM) compound or an agonist of TLR2.

32. The vaccine composition of claim 23 wherein the TLR agonist comprises an IRM compound, MALP-2, Pam3cys, LPS, polyIC, or a combination of the foregoing.

33. The vaccine composition of claim 24 wherein the TLR agonist comprises an IRM compound, MALP-2, Pam3cys, LPS, polyIC, CpG or a combination of the foregoing.

34. The vaccine composition of claim 23 wherein the TLR agonist comprises an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

35. The vaccine composition of claim 24 wherein the TLR agonist comprises an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

36. The vaccine composition of claim 23 wherein the at least one CD40 agonist comprises an anti-CD40 agonistic antibody.

37. The vaccine composition of claim 23 which is suitable for administration to a human subject in need of immunotherapy by a route selected from the group consisting of oral, nasal, topical, and injection.

38. The vaccine composition of claim 24 which is suitable for administration to a human subject in need of immunotherapy by a route selected from the group consisting of oral, nasal, topical, and injection.

39. The vaccine composition of claim 37 which is suitable for injection to a human subject in need of immunotherapy.

40. The vaccine composition of claim 38 which is suitable for injection to a human subject in need of immunotherapy.

41. The vaccine composition of claim 39 wherein injection is selected from the group consisting of subcutaneous, intravenous, intraperitoneal, intramuscular and intravenous.

42. The vaccine composition of claim 40 wherein injection is selected from the group consisting of subcutaneous, intravenous, intraperitoneal, intramuscular and intravenous.

43. The vaccine composition of claim 24 wherein the at least one TLR agonist comprises a TLR9 agonist.

44. The vaccine composition of claim 43 wherein the at least one TLR9 agonist comprises a CpG compound.

45. The vaccine composition of claim 23 wherein the at least one TLR agonist comprises an agonist of TLR7 or TLR8.

46. The vaccine composition of claim 24 wherein the at least one TLR agonist comprises an agonist of TLR7, TLR8 or TLR9.

47. The vaccine composition of claim 23 wherein the at least one TLR agonist comprises an agonist of TLR8.

48. The vaccine composition of claim 24 wherein the at least one TLR agonist comprises an agonist of TLR8.

49. The vaccine composition of claim 23 wherein the at least one TLR agonist comprises an agonist of TLR7.

50. The vaccine composition of claim 24 wherein the at least one TLR agonist comprises an agonist of TLR7.

51. A method of human immunotherapy which comprises administering to a human subject in need thereof an immunostimulatory composition according to claim 1 under conditions that elicit a synergistic effect on an immune response to an antigen.

52. A method of human immunotherapy which comprises administering to a human subject in need thereof an immunostimulatory composition according to claim 2 under conditions that elicit a synergistic effect on an immune response to an antigen.

53. The method of claim 51 wherein the immunostimulatory composition is administered via injection.

54. The method of claim 52 wherein the immunostimulatory composition is administered via injection.

55. The method of claim 53 wherein injection is selected from the group consisting of intraperitoneal, intramuscular, intravenous, and subcutaneous.

56. The method of claim 54 wherein injection is selected from the group consisting of intraperitoneal, intramuscular, intravenous, and subcutaneous.

57. The method of claim 51 wherein the administered immunostimulatory composition comprises a CD40 agonistic antibody or agonistic anti-CD40 antibody fragment.

58. The method of claim 51 wherein the administered immunostimulatory composition comprises an agonistic CD40L polypeptide or an agonistic CD40L polypeptide fragment.

59. The method of claim 52 wherein the at least one TLR agonist comprised in the administered immunostimulatory composition is selected from the group consisting of a TLR1, TLR2, TLR3, TLR4, TLR5, TLR6, TLR7, TLR8, and a TLR9 agonist.

60. The method of claim 51 wherein the administered immunostimulatory composition comprises at least one TLR7 or TLR8 agonist.

61. The method of claim 52 wherein the administered immunostimulatory composition comprises at least one TLR7, TLR8 or TLR9 agonist.

62. The method of claim 53 wherein the administered immunostimulatory composition comprises an agonistic an anti-4-1BB antibody or an agonistic anti-4-1BB antibody fragment or a 4-1BB ligand polypeptide.

63. A method of immunotherapy which comprises administering to a human subject in need thereof a vaccine composition according to claim 23 under conditions that elicit a synergistic increase in an immune response to an antigen.

64. A method of immunotherapy which comprises administering to a human subject in need thereof a vaccine composition according to claim 24 under conditions that elicit a synergistic increase in an immune response to an antigen.

65. The method of claim 63 wherein the vaccine composition is administered via an injection route.

66. The method of claim 64 wherein the vaccine composition is administered via an injection route.

67. The method of claim 65 wherein injection route is selected from the group consisting of intraperitoneal, intramuscular, intravenous, and subcutaneous.

68. The method of claim 66 wherein injection route is selected from the group consisting of intraperitoneal, intramuscular, intravenous, and subcutaneous.

69. The method of claim 63 wherein the administered vaccine composition comprises a CD40 agonistic antibody or agonistic anti-CD40 antibody fragment.

70. The method of claim 63 wherein the vaccine composition comprises a CD40L polypeptide or a CD40L polypeptide fragment.

71. The method of claim 64 wherein the administered vaccine comprises a TLR agonist selected from the group consisting of a TLR1, TLR2, TLR3, TLR4, TLR5, TLR6, TLR7, TLR8 and TLR9 agonist.

72. The method of claim 63 wherein the administered vaccine comprises a TLR7 or TLR8 agonist.

73. The method of claim 64 wherein the administered vaccine comprises a TLR7, TLR8 or TLR9 agonist.

74. The method of claim 64 wherein the administered vaccine comprises a TLR9 agonist.

75. The method of claim 64 wherein the administered vaccine comprises an anti-4-1BB agonistic antibody/or an agonistic anti-4-1BB antibody fragment.

76. The method of claim 63 wherein the administered vaccine comprises a tumor antigen, a viral antigen, a bacterial antigen, or a parasitic antigen.

77. The method of claim 64 wherein the administered vaccine comprises a tumor antigen, a viral antigen, a bacterial antigen, or a parasitic antigen.

\* \* \* \* \*